(12) United States Patent
Doyle

(10) Patent No.: US 10,213,550 B2
(45) Date of Patent: Feb. 26, 2019

(54) SYSTEMS AND METHODS FOR MONITORING CLINICAL PROCEDURES USING REGIONAL BLOOD OXYGEN SATURATION

(71) Applicant: Covidien LP, Mansfield, MA (US)

(72) Inventor: Peter Doyle, Vista, CA (US)

(73) Assignee: Covidien LP, Mansfield, MA (US)

( * ) Notice: Subject to any disclaimer, the term of this patent is extended or adjusted under 35 U.S.C. 154(b) by 746 days.

(21) Appl. No.: 14/602,179

(22) Filed: Jan. 21, 2015

(65) Prior Publication Data

US 2015/0205933 A1    Jul. 23, 2015

Related U.S. Application Data

(60) Provisional application No. 61/930,857, filed on Jan. 23, 2014.

(51) Int. Cl.
   *G06F 19/00*    (2018.01)
   *A61M 5/172*    (2006.01)

(52) U.S. Cl.
   CPC .......... *A61M 5/1723* (2013.01); *G06F 19/00* (2013.01); *G06F 19/3468* (2013.01); *A61M 2205/3306* (2013.01); *A61M 2205/3313* (2013.01); *A61M 2230/005* (2013.01); *A61M 2230/205* (2013.01)

(58) Field of Classification Search
   CPC ........ A61M 5/1723; A61M 2205/3306; A61M 2205/3313
   See application file for complete search history.

(56) References Cited

U.S. PATENT DOCUMENTS

| 4,280,494 A * | 7/1981 | Cosgrove, Jr. ...... A61M 5/1723 604/503 |
| 5,115,133 A | 5/1992 | Knudson |
| 5,187,672 A | 2/1993 | Chance et al. |

(Continued)

OTHER PUBLICATIONS

Tinker, J.H. and Michenfelder, J.D., "Sodium Nitroprusside: Pharmacology, Toxicology and Therapeutics," Anesthes, Sep. 1976; 45(3):340-54.

(Continued)

*Primary Examiner* — Nathan R Price
*Assistant Examiner* — Justin L Zamory
(74) *Attorney, Agent, or Firm* — Shumaker & Sieffert, P.A.

(57) ABSTRACT

Methods and systems are presented for monitoring a clinical procedure using regional blood oxygen saturation ($rSO_2$) of a subject. The $rSO_2$ of a subject is monitored, and clinical information is received, indicating that the subject is undergoing a clinical procedure (e.g., an infusion pump procedure for sodium nitroprusside administration). A change in the $rSO_2$ of the subject is detected, which may be indicative of a circulatory system impairment (e.g., elevated venous oxygen saturation) caused by the clinical procedure. Status information, which may be indicative of an increased risk of a physiological event (e.g., cyanide toxicity) is determined for the subject based on the clinical information and the detected change in the $rSO_2$ of the subject. Corrective actions may be triggered based on the status information in order to reduce the increased risk. The corrective actions may be implemented as smart prompt or closed loop systems.

20 Claims, 8 Drawing Sheets

(56) References Cited

U.S. PATENT DOCUMENTS

| | | |
|---|---|---|
| 5,222,495 A | 6/1993 | Clarke et al. |
| 5,277,181 A | 1/1994 | Mendelson et al. |
| 5,299,570 A | 4/1994 | Hatschek |
| 5,419,321 A | 5/1995 | Evans |
| 5,440,388 A | 8/1995 | Erickson |
| 5,482,034 A | 1/1996 | Lewis et al. |
| 5,661,302 A | 8/1997 | Evans et al. |
| 5,673,701 A | 10/1997 | Chance |
| 5,747,806 A | 5/1998 | Khalil et al. |
| 5,770,454 A | 6/1998 | Essenpreis et al. |
| 5,803,910 A | 9/1998 | Potratz |
| 5,820,558 A | 10/1998 | Chance |
| 5,825,488 A | 10/1998 | Kohl et al. |
| 5,830,132 A | 11/1998 | Robinson |
| 5,902,235 A * | 5/1999 | Lewis ................ A61B 5/14553 600/323 |
| 5,954,053 A | 9/1999 | Chance et al. |
| 5,983,122 A | 11/1999 | Jarman et al. |
| 6,058,324 A | 5/2000 | Chance |
| 6,122,535 A | 9/2000 | Kaestle et al. |
| 6,236,047 B1 | 5/2001 | Malin et al. |
| 6,278,889 B1 | 8/2001 | Robinson |
| 6,353,226 B1 | 3/2002 | Khalil et al. |
| 6,438,399 B1 | 8/2002 | Kurth |
| 6,549,795 B1 | 4/2003 | Chance |
| 6,615,061 B1 | 9/2003 | Khalil et al. |
| 6,615,065 B1 | 9/2003 | Barrett et al. |
| 6,708,048 B1 | 3/2004 | Chance |
| 6,819,950 B2 | 11/2004 | Mills |
| 7,098,037 B2 | 8/2006 | Haas et al. |
| 7,187,960 B2 | 3/2007 | Abreu |
| 7,271,912 B2 | 9/2007 | Sterling et al. |
| 7,315,752 B2 | 1/2008 | Kraemer et al. |
| 7,356,365 B2 | 4/2008 | Schurman |
| 7,424,317 B2 | 9/2008 | Parker et al. |
| 8,821,397 B2 | 9/2014 | Al-Ali et al. |
| 8,965,472 B2 | 2/2015 | Benni |
| 9,326,712 B1 | 5/2016 | Kiani |
| 2008/0108884 A1 * | 5/2008 | Kiani ................ A61B 5/0002 600/301 |
| 2008/0194924 A1 * | 8/2008 | Valk ................ A61M 5/1723 600/301 |
| 2008/0228053 A1 | 9/2008 | Wang et al. |
| 2011/0208024 A1 | 8/2011 | Widman et al. |
| 2014/0371548 A1 | 12/2014 | Al-Ali et al. |
| 2015/0099950 A1 | 4/2015 | Al-Ali et al. |

OTHER PUBLICATIONS

Funk, M. et al., "Lower Limb Ischemia Related to use of the Intra-Aortic Balloon Pump," Heart and Lung: The Journal of Critical Care. Dec. 1989,18(6):542-552.

Rathore, Y.S. et al., "Monitored Gradual Occlusion of the Internal Carotid Artery Followed by Ligation for Giant Internal Carotid Artery Aneurysms," Neurol India [serial online] 2012 [cited Sep. 5, 2013];60:174-179. Available from: http://www.neurologyindia.com/text.asp?2012/60/2/174/96396.

Allen, J., "Photoplethysmography and its Application in Clinical Physiological Measurement," Physiol. Meas., vol. 28, Mar. 2007, pp. R1-R39.

Murray, W. B., and Foster, P. A., "The Peripheral Pulse Wave: Information Overlooked," J. Clin. Monit., vol. 12, Sep. 1996, pp. 365-377.

Shelley, K. H., "Photoplethysmography: Beyond the Calculation of Arterial Oxygen Saturation and Heart Rate," Anesth. Analg., vol. 105, Dec. 2007, pp. S31-S36.

* cited by examiner

SYSTEMS AND METHODS FOR MONITORING CLINICAL PROCEDURES USING REGIONAL BLOOD OXYGEN SATURATION

CROSS REFERENCE TO RELATED APPLICATION

This application claims the benefit of U.S. Provisional Application No. 61/930,857, filed Jan. 23, 2014, which is hereby incorporated by reference herein in its entirety.

SUMMARY

The present disclosure relates to monitoring clinical procedures using regional blood oxygen saturation ($rSO_2$), and more particularly, relates to monitoring an infusion pump procedure for sodium nitroprusside administration using $rSO_2$, monitoring a carotid artery clamp procedure using $rSO_2$, and monitoring an intra-aorta balloon pump procedure using $rSO_2$.

Methods and systems are provided for monitoring clinical procedures using $rSO_2$ of a subject. In some embodiments, a system monitors an infusion pump procedure for sodium nitroprusside administration by detecting changes in the $rSO_2$ of a region of tissue. In some embodiments, a system monitors a carotid artery clamp procedure by detecting changes in the $rSO_2$ of a region of tissue. In some embodiments, a system monitors an intra-aorta balloon pump procedure by detecting changes in the $rSO_2$ of a region of a tissue.

In some embodiments, a physiological monitoring system includes light drive circuitry configured for generating a light drive signal configured to cause one or more light sources to emit a plurality of light signals, where the plurality of light signals corresponds to a plurality of wavelengths of light. The system further includes one or more signal inputs configured for receiving a first plurality of light signals that have been attenuated by a first region of a subject, where the first plurality of light signals corresponds to the plurality of wavelengths of light, receiving a second plurality of light signals that have been attenuated by a second region of the subject, where the second plurality of light signals corresponds to the plurality of wavelengths of light and receiving clinical information associated with the subject undergoing an infusion pump procedure for sodium nitroprusside administration. The system further includes one or more processors configured for monitoring regional blood oxygen saturation ($rSO_2$) of the subject based on the first received plurality of light signals and the second received plurality of light signals and detecting a change in the $rSO_2$ of the subject. The one or more processors are further configured for determining status information for the subject based on the clinical information and the detected change in the $rSO_2$ of the subject and triggering an action based on the status information.

In some embodiments, a method for triggering an action is provided. The method includes generating a light drive signal configured to cause one or more light sources to emit a plurality of light signals, where the plurality of light signals corresponds to a plurality of wavelengths of light. The method further includes receiving a first plurality of light signals that have been attenuated by a first region of a subject, where the first plurality of light signals corresponds to the plurality of wavelengths of light, and receiving a second plurality of light signals that have been attenuated by a second region of the subject, where the second plurality of light signals corresponds to the plurality of wavelengths of light. The method further includes monitoring regional blood oxygen saturation ($rSO_2$) of the subject based on the first received plurality of light signals and the second received plurality of light signals. The method further includes receiving clinical information associated with the subject undergoing an infusion pump procedure for sodium nitroprusside administration and detecting a change in the $rSO_2$ of the subject. The method further includes determining status information for the subject based on the clinical information and the detected change in the $rSO_2$ of the subject and triggering an action based on the status information.

In some embodiments, a physiological monitoring system includes a signal input configured for receiving clinical information associated with a subject undergoing a clinical procedure, where the clinical procedure affects the circulatory system of the subject. The system further include one or more processors configured for monitoring regional blood oxygen saturation ($rSO_2$) in a region of the subject that is affected by the clinical procedure and detecting one or more changes in the $rSO_2$ in the region of the subject. The one or more processors are further configured for determining status information associated with the subject based on the one or more changes in the $rSO_2$ in the region of the subject and the clinical information and triggering an action based on the status information.

In some embodiments, a method for triggering an action is provided. The method includes receiving clinical information associated with a subject undergoing a clinical procedure, where the clinical procedure affects the circulatory system of the subject. The method further includes monitoring regional blood oxygen saturation ($rSO_2$) in a region of the subject that is affected by the clinical procedure and detecting one or more changes in the $rSO_2$ in the region of the subject. The method further includes determining status information associated with the subject based on the one or more changes in the $rSO_2$ in the region of the subject and the clinical information and triggering an action based on the status information.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
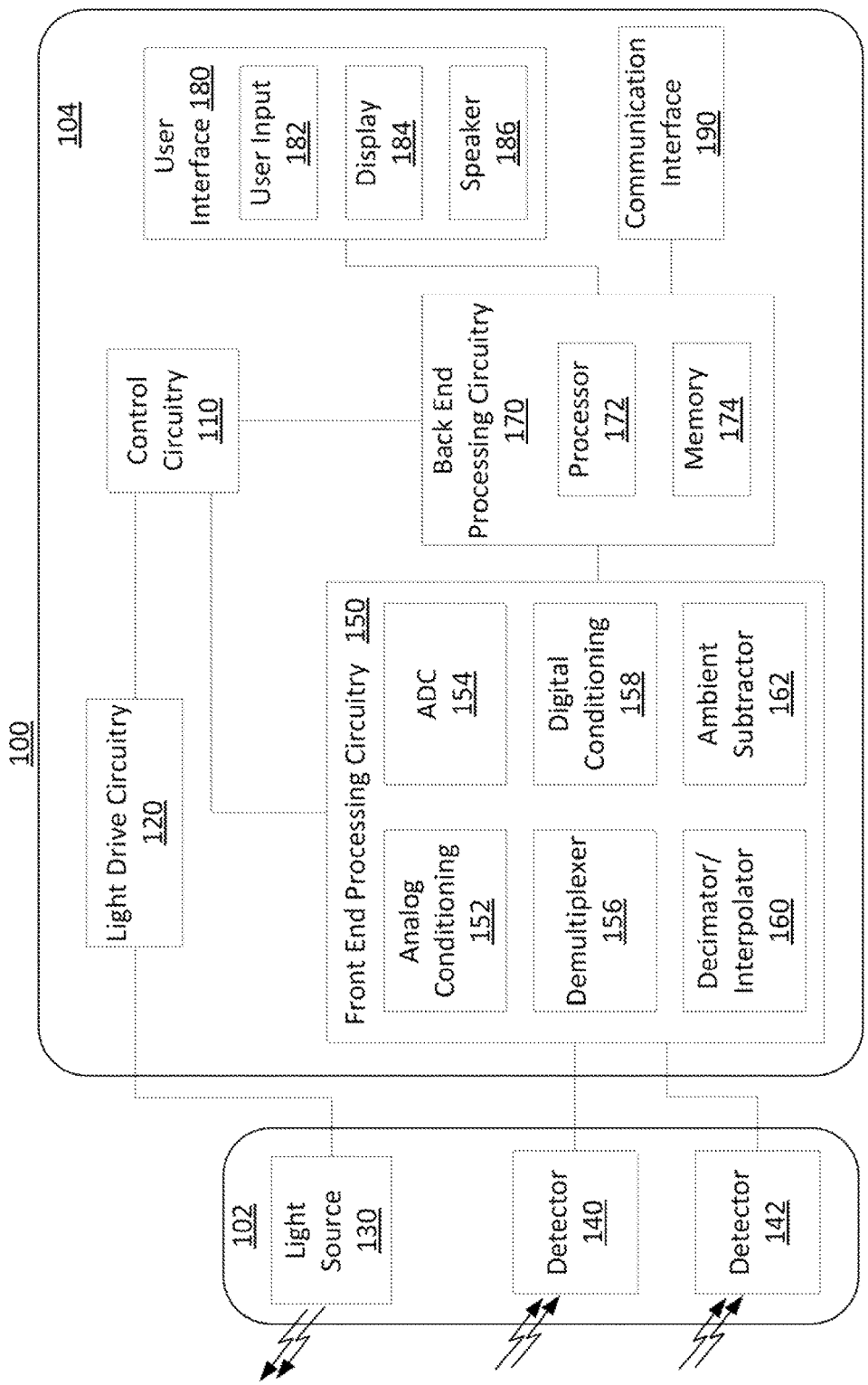
FIG. 1 is a block diagram of an illustrative physiological monitoring system in accordance with some embodiments of the present disclosure.

The present disclosure is directed towards monitoring a clinical procedure that a subject is undergoing using the $rSO_2$ of the subject. In some embodiments, the physiological monitoring system of the present disclosure may be a regional oximetry system. The $rSO_2$ of a region of a subject's tissue is monitored, and clinical information is received, indicating that the subject is undergoing a clinical procedure (e.g., an infusion pump procedure for sodium nitroprusside administration). A change in the $rSO_2$ of the subject is detected, which may be indicative of a circulatory system impairment (e.g., elevated venous oxygen saturation) caused by the clinical procedure. Status information, which may be indicative of an increased risk of a physiological event (e.g., cyanide toxicity), is determined for the subject based on the clinical information and the detected change in the $rSO_2$ of the subject. One or more corrective actions may be triggered, based on the status information, in order to reduce the increased risk, and the one or more corrective actions may be provided to the user by a smart prompt system or automatically performed by a closed loop system. Monitoring a clinical procedure by detecting changes in $rSO_2$ corresponding to indications of circulatory system impairment may permit early detection and efficient correction of circulatory problems caused by the clinical procedure.

In some embodiments, a change in the $rSO_2$ of a subject may be indicative of a change in venous oxygen saturation. In some embodiments, a change in the $rSO_2$ of a subject may be indicative of a change in the tissue perfusion of a region of a subject's tissue (e.g., cerebral tissue). In some embodiments, the system may monitor a clinical procedure that is associated with a risk of detrimentally affecting venous oxygen saturation or tissue perfusion. For example, clinical procedures may include an infusion pump procedure for sodium nitroprusside administration, a carotid artery clamp procedure, and an intra-aorta balloon pump procedure.

The foregoing techniques may be implemented in an oximeter. An oximeter is a medical device that may determine the oxygen saturation of an analyzed tissue. One common type of oximeter is a regional oximeter. A regional oximeter is used to estimate the blood oxygen saturation in a region of a subject's tissue. The regional oximeter may compute a differential absorption value for each of two or more wavelengths of light received at two different locations on the subject's body to estimate the regional blood oxygen saturation of hemoglobin in a region of the subject's tissue. For each wavelength of light, the regional oximeter may compare the amount of light absorbed by the subject's tissue in a first region to the amount of light absorbed by the subject's tissue in a second region to derive the differential absorption values. As opposed to pulse oximetry, which typically examines the oxygen saturation of pulsatile, arterial tissue, regional oximetry examines the oxygen saturation of blood in a region of tissue that may include blood in the venous, arterial, and capillary systems. For example, a regional oximeter may include a sensor unit configured for placement on a subject's forehead and may be used to estimate the blood oxygen saturation of a region of tissue beneath the sensor unit (e.g., cerebral tissue).

In some embodiments, the oximeter may be a combined oximeter including a regional oximeter and a pulse oximeter. A pulse oximeter is a device for non-invasively measuring the oxygen saturation of a patient's blood (as opposed to measuring oxygen saturation directly by analyzing a blood sample taken from the patient). Regional, pulse, and combined oximeters may be included in patient monitoring systems that measure and display various blood flow characteristics including, but not limited to, the regional oxygen saturation of a region of tissue and the oxygen saturation of hemoglobin in arterial blood. Such patient monitoring systems may also measure and display additional physiological parameters, such as a patient's pulse rate, respiration rate, respiration effort, blood pressure, any other suitable physiological parameter, or any combination thereof. Such patient monitoring systems may also monitor clinical procedures the patient is undergoing, including, for example, an infusion pump procedure, a carotid artery clamp procedure, an intra-aorta balloon pump procedure, any other suitable clinical procedure that affects the circulatory system, or any combination thereof. Regional and pulse oximetry may be implemented using a photoplethysmograph. Pulse oximeters and other photoplethysmograph devices may also be used to determine other physiological parameters and information as disclosed in: J. Allen, "Photoplethysmography And its Application in Clinical Physiological Measurement," *Physiol. Meas.*, vol. 28, pp. R1-R39, March 2007; W. B. Murray and P. A. Foster, "The Peripheral Pulse Wave: Information Overlooked," *J. Clin. Monit.*, vol. 12, pp. 365-377, September 1996; and K. H. Shelley, "Photoplethysmography: Beyond the Calculation of Arterial Oxygen Saturation and Heart Rate," *Anesth. Analg.*, vol. 105, pp. S31-S36, December 2007; all of which are incorporated by reference herein in their entireties.

An oximeter may include a light sensor that is placed at a site on a patient, typically a fingertip, toe, forehead or earlobe, or in the case of a neonate, across a foot or hand. The oximeter may use a light source to pass light through blood perfused tissue and photoelectrically sense the absorption of the light in the tissue. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, around or in front of the ear, locations with strong pulsatile arterial flow, and locations above tissue desired to be monitored. Suitable sensors for these locations may include sensors that detect reflected light.

The oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, an inverted signal, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof.

The light intensity or the amount of light absorbed may then be used to calculate any of a number of physiological parameters, including an amount of a blood constituent (e.g., oxyhemoglobin) being measured as well as a pulse rate and when each individual pulse occurs.

In some embodiments, the photonic signal interacting with the tissue is of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The system may process data to determine physiological parameters using techniques well known in the art. For example, the system may determine blood oxygen saturation using two wavelengths of light and a ratio-of-ratios calculation. In another example, the system may determine regional blood oxygen saturation using multiple wavelengths of light and a differential absorption technique. The system also may identify pulses and determine pulse amplitude, respiration, blood pressure, other suitable parameters, or any combination thereof, using any suitable calculation techniques. In some embodiments, the system may use information from external sources (e.g., tabulated data, secondary sensor devices) to determine physiological parameters.

In some embodiments, the regional oximeter may include a first sensor located at a first distance from the light source (e.g., the near detector) and a second sensor located at a second farther distance from the light source (e.g., the far detector). In some embodiments, the regional oximeter may include a near detector at a distance of 3 centimeters (cm) and a far detector at a distance of 4 cm from the light source, which may include, for example, one or more emitters. The distance between each detector and the light source affects the mean path length of the detected light and thus the depth of tissue through which the respective received wavelength of light passes. In other words, the light detected by the near detector may pass through shallow, superficial tissue, whereas the light detected by the far detector may pass through additional, deep tissue. In some embodiments, the regional oximeter's light source may include two or more emitters and one or more detectors. For example, a first emitter may be located a short distance from a detector, and the second emitter may be located a longer distance from the detector.

In some embodiments, multiple wavelengths of light may be received at both the near and far detectors, and the absorption of the multiple wavelengths of light may be computed and contrasted at each detector to derive regional blood oxygen saturation. For example, light signals for four wavelengths of light may be received at each of the near and far detectors, and the amount of light of each wavelength received at the near detector may be subtracted from the amount of light of each wavelength received at the far detector. In some embodiments, the amount of absorption computed at the near detector for each wavelength may be subtracted from the corresponding amount of the absorption computed at the far detector. The resulting light signals or absorptions may be used to compute the regional blood oxygen saturation of a region of deep tissue through which light received at the far detector passed. Because the far detector receives light that passes through deep tissue in addition to the shallow tissue through which the light passes and is received at the near detector, the regional saturation may be computed for just the deep tissue by subtracting out the amount of light received by the near detector or the corresponding absorption. For example, a regional oximeter on a subject's forehead may include near and far detectors spaced from the light source such that the near detector receives light that passes through the subject's forehead tissue, including the superficial skin, shallow tissue covering the skull, and the skull, and the far detector receives light that passes through the forehead tissue and brain tissue (i.e., cerebral tissue). In the example, the differences in the amounts of light received by the near and far detectors may be used to derive an estimate of the regional blood oxygen saturation of the subject's cerebral tissue (i.e., cerebral blood oxygen saturation).

The following description and accompanying FIGS. 1-8 provide additional details and features of some embodiments of the present disclosure.

FIG. 1 is a block diagram of an illustrative physiological monitoring system 100 in accordance with some embodiments of the present disclosure. System 100 may include a sensor 102 and a monitor 104 for generating and processing physiological signals of a subject. In some embodiments, sensor 102 and monitor 104 may be part of an oximeter.

Sensor 102 of physiological monitoring system 100 may include light source 130, detector 140, and detector 142. Light source 130 may be configured to emit photonic signals having two or more wavelengths of light (e.g., red and IR) into a subject's tissue. For example, light source 130 may include a red light emitting light source and an IR light emitting light source, (e.g., red and IR light emitting diodes (LEDs)), for emitting light into the tissue of a subject to generate physiological signals. In one embodiment, the red wavelength may be between about 600 nm and about 700 nm, and the IR wavelength may be between about 800 nm and about 1000 nm. It will be understood that light source 130 may include any number of light sources with any suitable characteristics. In embodiments where an array of sensors is used in place of single sensor 102, each sensor may be configured to emit a single wavelength. For example, a first sensor may emit only a red light while a second may emit only an IR light. In some embodiments, light source 130 may be configured to emit two or more wavelengths of near-infrared light (e.g., wavelengths between 600 nm and 1000 nm) into a subject's tissue. In some embodiments, light source 130 may be configured to emit four wavelengths of light (e.g., 724 nm, 770 nm, 810 nm, and 850 nm) into a subject's tissue.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detectors 140 and 142 may be chosen to be specifically sensitive to the chosen targeted energy spectrum of light source 130.

In some embodiments, detectors 140 and 142 may be configured to detect the intensity of multiple wavelengths of near-infrared light. In some embodiments, detectors 140 and 142 may be configured to detect the intensity of light at the red and IR wavelengths. In some embodiments, an array of sensors may be used and each sensor in the array may be configured to detect an intensity of a single wavelength. In operation, light may enter detector 140 after passing through the subject's tissue, including skin, bone, and other shallow tissue (e.g., non-cerebral tissue and shallow cerebral tissue). Light may enter detector 142 after passing through the subject's tissue, including skin, bone, other shallow tissue (e.g., non-cerebral tissue and shallow cerebral tissue), and deep tissue (e.g., deep cerebral tissue). Detectors 140 and 142 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 140 and 142. After converting the received light to an electrical signal, detectors 140 and 142 may send the detection signals to monitor 104, where the detection signals may be processed and physiological parameters may be determined (e.g., based on the absorption of the red and IR wavelengths in the subject's tissue at both detectors). In some embodiments, one or more of the detection signals may be preprocessed by sensor 102 before being transmitted to monitor 104.

In the embodiment shown, monitor 104 includes control circuitry 110, light drive circuitry 120, front end processing circuitry 150, back end processing circuitry 170, user interface 180, and communication interface 190. Monitor 104 may be communicatively coupled to sensor 102 using, for example, one or more signal inputs.

Control circuitry 110 may be coupled to light drive circuitry 120, front end processing circuitry 150, and back end processing circuitry 170, and may be configured to control the operation of these components. In some embodiments, control circuitry 110 may be configured to provide timing control signals to coordinate their operation. For example, light drive circuitry 120 may generate one or more light drive signals, which may be used to turn on and off the light source 130, based on the timing control signals. The front end processing circuitry 150 may use the timing control signals to operate synchronously with light drive circuitry 120. For example, front end processing circuitry 150 may synchronize the operation of an analog-to-digital converter and a demultiplexer with the light drive signal based on the timing control signals. In addition, the back end processing circuitry 170 may use the timing control signals to coordinate its operation with front end processing circuitry 150.

Light drive circuitry 120, as discussed above, may be configured to generate a light drive signal that is provided to light source 130 of sensor 102. The light drive signal may, for example, control the intensity of light source 130 and the timing of when light source 130 is turned on and off. In some embodiments, light drive circuitry 120 may comprise a power supply and a switch for selectively applying power to light source 130. When light source 130 is configured to emit two or more wavelengths of light, the light drive signal may be configured to control the operation of each wavelength of light. The light drive signal may comprise a single signal or may comprise multiple signals (e.g., one signal for each wavelength of light). In some embodiments, light drive circuitry 130 provides one or more light drive signals to light source 130.

Figure 2A:
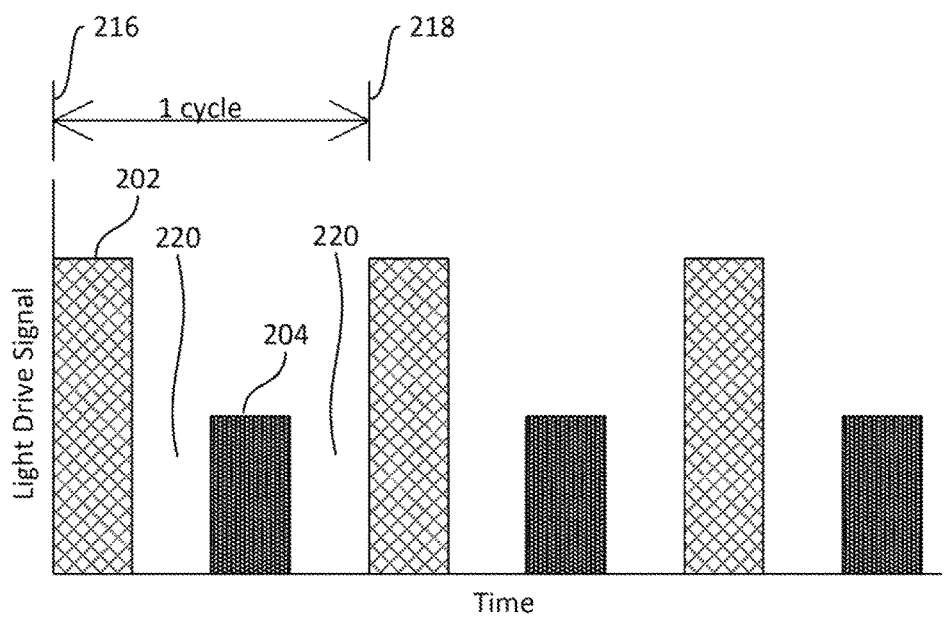
FIG. 2A shows an illustrative plot of a light drive signal in accordance with some embodiments of the present disclosure.

FIG. 2A shows an illustrative plot of a light drive signal including red light drive pulse 202 and IR light drive pulse 204 in accordance with some embodiments of the present disclosure. In the illustrated embodiment, light drive pulses 202 and 204 are shown as square waves. It will be understood that square waves are presented merely as an illustrative example, not by way of limitation, and that these pulses may include any other suitable signal, for example, shaped pulse waveforms, rather than a square waves. The shape of the pulses may be generated by a digital signal generator, digital filters, analog filters, any other suitable equipment, or any combination thereof. For example, light drive pulses 202 and 204 may be generated by light drive circuitry 120 under the control of control circuitry 110. As used herein, drive pulses may refer to the high and low states of a pulse, switching power or other components on and off, high and low output states, high and low values within a continuous modulation, other suitable relatively distinct states, or any combination thereof. The light drive signal may be provided to light source 130, including red light drive pulse 202 and IR light drive pulse 204 to drive red and IR light emitters, respectively, within light source 130.

Red light drive pulse 202 may have a higher amplitude than IR light drive 204 since red LEDs may be less efficient than IR LEDs at converting electrical energy into light energy. In some embodiments, the output levels may be equal, may be adjusted for nonlinearity of emitters, may be modulated in any other suitable technique, or any combination thereof. Additionally, red light may be absorbed and scattered more than IR light when passing through perfused tissue.

When the red and IR light sources are driven in this manner they emit pulses of light at their respective wavelengths into the tissue of a subject in order generate physiological signals that physiological monitoring system 100 may process to calculate physiological parameters. It will be understood that the light drive amplitudes of FIG. 2A are merely exemplary and that any suitable amplitudes or combination of amplitudes may be used, and may be based on the light sources, the subject tissue, the determined physiological parameter, modulation techniques, power sources, any other suitable criteria, or any combination thereof. It will also be understood that in systems that use more than two wavelengths of light, additional light drive pulses may be included in the light drive signal. For example, when four wavelengths of light are used, four light drive pulses, one for each wavelength of light, may be included in the light drive signal.

The light drive signal of FIG. 2A may also include "off" periods 220 between the red and IR light drive pulse. "Off" periods 220 are periods during which no drive current may be applied to light source 130. "Off" periods 220 may be provided, for example, to prevent overlap of the emitted light, since light source 130 may require time to turn completely on and completely off. The period from time 216 to time 218 may be referred to as a drive cycle, which includes four segments: a red light drive pulse 202, followed by an "off" period 220, followed by an IR light drive pulse 204, and followed by an "off" period 220. After time 218, the drive cycle may be repeated (e.g., as long as a light drive signal is provided to light source 130). It will be understood that the starting point of the drive cycle is merely illustrative and that the drive cycle can start at any location within FIG. 2A, provided the cycle spans two drive pulses and two "off" periods. Thus, each red light drive pulse 202 and each IR light drive pulse 204 may be understood to be surrounded by two "off" periods 220. "Off" periods may also be referred to as dark periods, in that the emitters are dark or returning to dark during that period. It will be understood that the particular square pulses illustrated in FIG. 2A are merely exemplary and that any suitable light drive scheme is possible. For example, light drive schemes may include shaped pulses, sinusoidal modulations, time division multiplexing other than as shown, frequency division multiplexing, phase division multiplexing, any other suitable light drive scheme, or any combination thereof.

Referring back to FIG. 1, front end processing circuitry 150 may receive detection signals from detectors 140 and 142 and provide two or more processed signals to back end processing circuitry 170. In some embodiments, front end processing circuitry 150 may receive the detection signals from one or more signal inputs of monitor 104. The term "detection signals," as used herein, may refer to any of the signals generated within front end processing circuitry 150 as it processes the output signal of detectors 140 and 142. Front end processing circuitry 150 may perform various analog and digital processing of the detector signals. One suitable detector signal that may be received by front end processing circuitry 150 is shown in FIG. 2B.

Figure 2B:
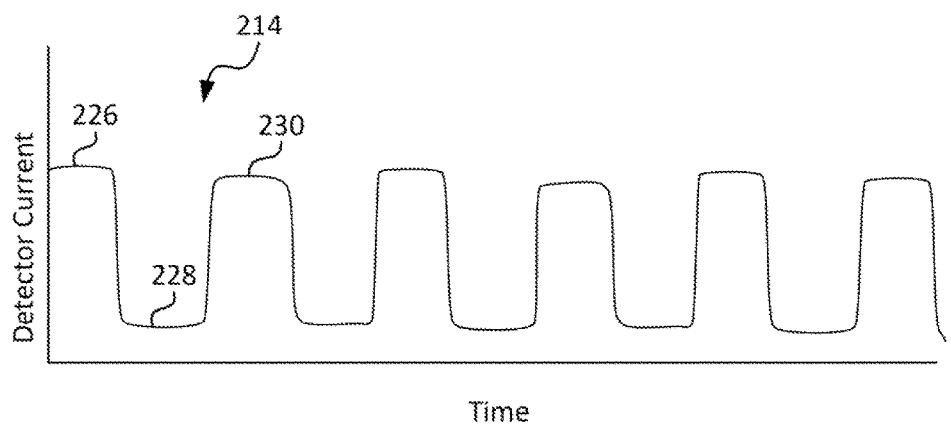
FIG. 2B shows an illustrative plot of a detector signal that may be generated by a sensor in accordance with some embodiments of the present disclosure.

FIG. 2B shows an illustrative plot of detector current waveform 214 that may be generated by a sensor in accordance with some embodiments of the present disclosure. The peaks of detector current waveform 214 may represent current signals provided by a detector, such as detectors 140 and 142 of FIG. 1, when light is being emitted from a light source. The amplitude of detector current waveform 214 may be proportional to the light incident upon the detector. The peaks of detector current waveform 214 may be synchronous with drive pulses driving one or more emitters of a light source, such as light source 130 of FIG. 1. For example, detector current peak 226 may be generated in response to a light source being driven by red light drive pulse 202 of FIG. 2A, and peak 230 may be generated in response to a light source being driven by IR light drive pulse 204. Valley 228 of detector current waveform 214 may be synchronous with periods of time during which no light is being emitted by the light source, or the light source is returning to dark, such as "off" period 220. While no light is being emitted by a light source during the valleys, detector current waveform 214 may not fall all the way to zero.

It will be understood that detector current waveform 214 may be an at least partially idealized representation of a detector signal, assuming perfect light signal generation, transmission, and detection. It will be understood that an actual detector current will include amplitude fluctuations, frequency deviations, droop, overshoot, undershoot, rise time deviations, fall time deviations, other deviations from the ideal, or any combination thereof. It will be understood that the system may shape the drive pulses shown in FIG. 2A in order to make the detector current as similar as possible to idealized detector current waveform 214.

Referring back to FIG. 1, front end processing circuitry 150, which may receive detection signals, such as detector current waveform 214, may include analog conditioning 152, analog-to-digital converter (ADC) 154, demultiplexer 156, digital conditioning 158, decimator/interpolator 160, and ambient subtractor 162.

Analog conditioning 152 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof.

The conditioned analog signals may be processed by analog-to-digital converter 154, which may convert the conditioned analog signals into digital signals. Analog-to-digital converter 154 may operate under the control of control circuitry 110. Analog-to-digital converter 154 may use timing control signals from control circuitry 110 to determine when to sample the analog signal. Analog-to-digital converter 154 may be any suitable type of analog-to-digital converter of sufficient resolution to enable a physiological monitor to accurately determine physiological parameters. In some embodiments, analog-to-digital converter 154 may be a two channel analog-to-digital converter, where each channel is used for a respective detector waveform.

Demultiplexer 156 may operate on the analog or digital form of the detector signals to separate out different components of the signals. For example, detector current waveform 214 of FIG. 2B includes a red component corresponding to peak 226, an IR component corresponding to peak 230, and at least one ambient component corresponding to valley 228. Demultiplexer 156 may operate on detector current waveform 214 of FIG. 2B to generate a red signal, an IR signal, a first ambient signal (e.g., corresponding to the ambient component corresponding to valley 228 that occurs immediately after the peak 226), and a second ambient signal (e.g., corresponding to the ambient component corresponding to valley 228 that occurs immediately after the IR component 230). Demultiplexer 156 may operate under the control of control circuitry 110. For example, demultiplexer 156 may use timing control signals from control circuitry 110 to identify and separate out the different components of the detector signals.

Digital conditioning 158 may perform any suitable digital conditioning of the detector signals. Digital conditioning 158 may include any type of digital filtering of the signal (e.g., low pass, high pass, band pass, notch, averaging, or any other suitable filtering), amplifying, performing an operation on the signal, performing any other suitable digital conditioning, or any combination thereof.

Decimator/interpolator 160 may decrease the number of samples in the digital detector signals. For example, decimator/interpolator 160 may decrease the number of samples by removing samples from the detector signals or replacing samples with a smaller number of samples. The decimation or interpolation operation may include or be followed by filtering to smooth the output signal.

Ambient subtractor 162 may operate on the digital signal. In some embodiments, ambient subtractor 162 may remove dark or ambient contributions to the received signal.

The components of front end processing circuitry 150 are merely illustrative and any suitable components and combinations of components may be used to perform the front end processing operations.

The front end processing circuitry 150 may be configured to take advantage of the full dynamic range of analog-to-digital converter 154. This may be achieved by applying gain to the detection signals by analog conditioning 152 to map the expected range of the detection signals to the full or close to full output range of analog-to-digital converter 154. The output value of analog-to-digital converter 154, as a function of the total analog gain applied to each of the detection signals, may be given as:

ADC Value=Total Analog Gain×[Ambient Light+ LED Light]

Ideally, when ambient light is zero and when the light source is off, the analog-to-digital converter 154 will read just above the minimum input value. When the light source is on, the total analog gain may be set such that the output of analog-to-digital converter 154 may read close to the full scale of analog-to-digital converter 154 without saturating. This may allow the full dynamic range of analog-to-digital converter 154 to be used for representing the detection signals, thereby increasing the resolution of the converted signal. In some embodiments, the total analog gain may be reduced by a small amount so that small changes in the light levels incident on the detectors do not cause saturation of analog-to-digital converter 154.

However, if the contribution of ambient light is large relative to the contribution of light from a light source, the total analog gain applied to the detection current may need to be reduced to avoid saturating analog-to-digital converter 154. When the analog gain is reduced, the portion of the signal corresponding to the light source may map to a smaller number of analog-to-digital conversion bits. Thus, more ambient light noise in the input of analog-to-digital converter 154 may result in fewer bits of resolution for the portion of the signal from the light source. This may have a detrimental effect on the signal-to-noise ratio of the detection signals. Accordingly, passive or active filtering or signal modification techniques may be employed to reduce the effect of ambient light on the detection signals that are applied to analog-to-digital converter 154, and thereby reduce the contribution of the noise component to the converted digital signal.

Back end processing circuitry 170 may include processor 172 and memory 174. Processor 172 may be adapted to execute software, which may include an operating system and one or more applications, as part of performing the functions described herein. Processor 172 may receive and further process physiological signals received from front end processing circuitry 150. For example, processor 172 may determine one or more physiological parameters based on the received physiological signals. Processor 172 may include an assembly of analog or digital electronic components. Processor 172 may calculate physiological information. For example, processor 172 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof. Processor 172 may perform any suitable signal processing of a signal, such as any suitable band-pass filtering, adaptive filtering, closed-loop filtering, any other suitable filtering, and/or any combination thereof. Processor 172 may also receive input signals from additional sources not shown. For example, processor 172 may receive an input signal containing information about treatments provided to the subject from user interface 180. Additional input signals may be used by processor 172 in any of the calculations or operations it performs in accordance with back end processing circuitry 170 or monitor 104.

Memory 174 may include any suitable computer-readable media capable of storing information that can be interpreted by processor 172. In some embodiments, memory 174 may store clinical procedure information, predetermined thresholds, calculated values, such as regional blood oxygen saturation, blood oxygen saturation, pulse rate, blood pressure, fiducial point locations or characteristics, initialization parameters, any other calculated values, or any combination thereof, in a memory device for later retrieval. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuitry 170 may be communicatively coupled with user interface 180 and communication interface 190.

User interface 180 may include user input 182, display 184, and speaker 186. User interface 180 may include, for example, any suitable device such as one or more medical devices (e.g., a medical monitor that displays various physiological parameters, a medical alarm, or any other suitable medical device that either displays physiological parameters or uses the output of back end processing 170 as an input), one or more display devices (e.g., monitor, personal digital assistant (PDA), mobile phone, tablet computer, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments, and so forth.

In an embodiment, the subject may be a medical patient and display 184 may exhibit a list of values which may generally apply to the subject, such as, for example, age ranges or medication families, which the user may select using user input 182. Additionally, display 184 may display, for example, clinical procedure status, operator prompts, a subject's regional oxygen saturation generated by monitor 104 (referred to as an "rSO$_2$" measurement), a subject's blood oxygen saturation generated by monitor 104 (referred to as an "SpO$_2$" measurement), an estimate of a subject's venous oxygen saturation generated by monitor 104 (referred to as an "S$_v$O$_2$" measurement), status information, clinical information, pulse rate information, respiration rate information, blood pressure, any other parameters, and any combination thereof. Display 184 may include any type of display such as a cathode ray tube display, a flat panel display such a liquid crystal display (LCD), LED display, or plasma display, or any other suitable display device. Speaker 186 within user interface 180 may provide an audible sound that may be used in various embodiments, such as for example, sounding an audible alarm in the event that a patient's physiological parameters are not within a predefined normal range.

Communication interface 190 may enable monitor 104 to exchange information with external devices, such as infusion pumps and other systems that contain surgical procedure data such as sodium nitroprusside administration data, carotid artery clamp procedure data, and intra-aorta balloon pump procedure data. In some embodiments, communication interface 190 may enable monitor 104 to control external devices. Communications interface 190 may include any suitable hardware, software, or both, which may allow monitor 104 to communicate with electronic circuitry, a device, a network, a server or other workstations, a display, or any combination thereof. Communications interface 190 may include one or more receivers, transmitters, transceivers, antennas, plug-in connectors, ports, signal inputs, communications buses, communications protocols, device identification protocols, any other suitable hardware or software, or any combination thereof. Communications interface 190 may be configured to allow wired communication (e.g., using USB, RS-232, Ethernet, or other standards), wireless communication (e.g., using WiFi, IR, WiMax, BLUETOOTH, USB, or other standards), or both. For example, communications interface 190 may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, communications interface 190 may include an internal bus such as, for example, one or more slots for insertion of expansion cards.

It will be understood that the components of physiological monitoring system 100 that are shown and described as separate components are shown and described as such for illustrative purposes only. In some embodiments the functionality of some of the components may be combined in a single component. For example, the functionality of front end processing circuitry 150 and back end processing circuitry 170 may be combined in a single processor system. Additionally, in some embodiments the functionality of some of the components of monitor 104 shown and described herein may be divided over multiple components. For example, some or all of the functionality of control circuitry 110 may be performed in front end processing circuitry 150, in back end processing circuitry 170, or both. In addition, while a single processor is depicted in FIG. 1, it will be understood that one or more processors may be used to perform the functionality described above. In other embodiments, the functionality of one or more of the components may be performed in a different order or may not be required. In an embodiment, all of the components of physiological monitoring system 100 can be realized in processor circuitry.

Figure 3:
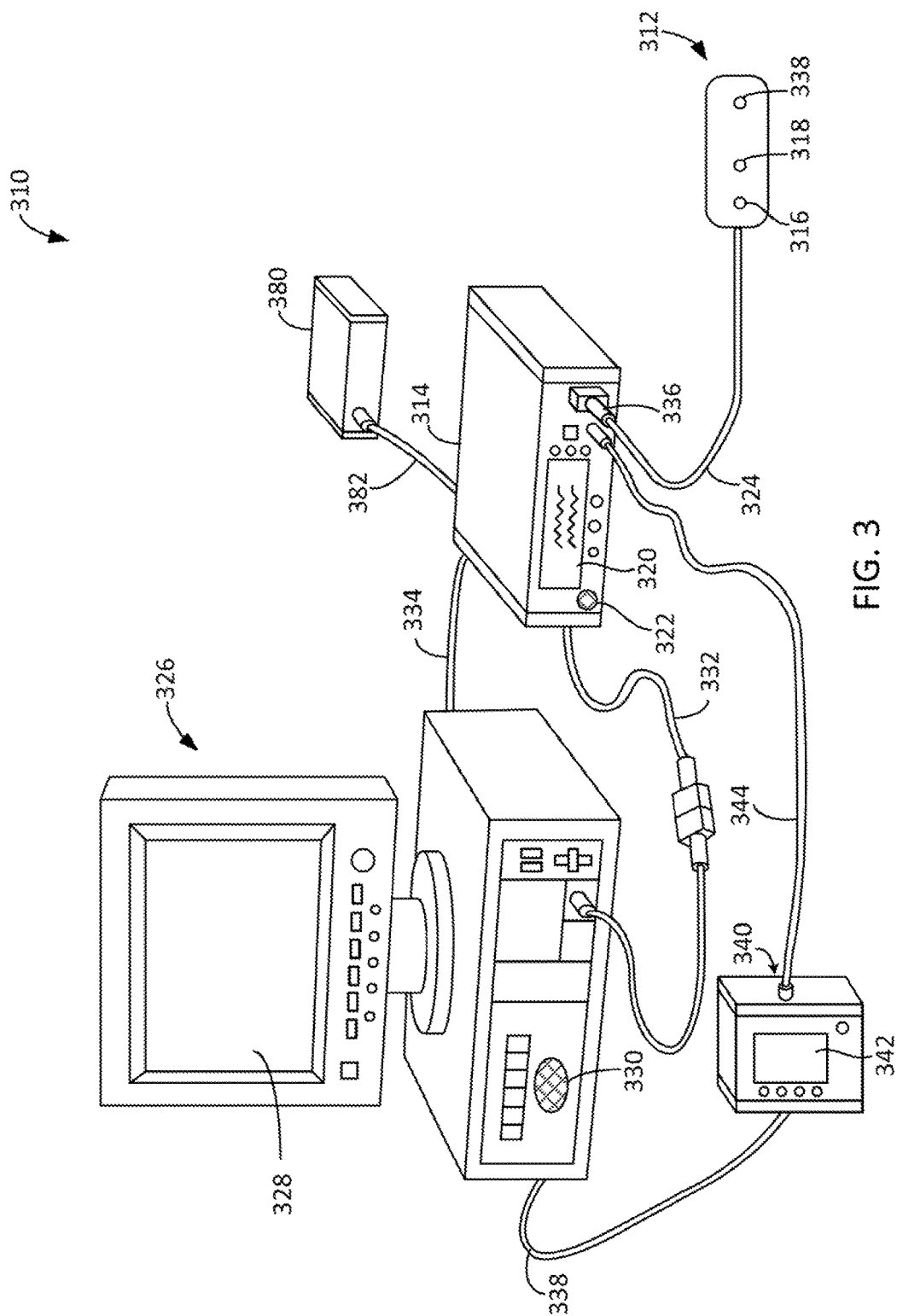
FIG. 3 is a perspective view of an illustrative physiological monitoring system in accordance with some embodiments of the present disclosure.

FIG. 3 is a perspective view of an illustrative physiological monitoring system 310 in accordance with some embodiments of the present disclosure. In some embodiments, one or more components of physiological monitoring system 310 may include one or more components of physiological monitoring system 100 of FIG. 1. Physiological monitoring system 310 may include sensor unit 312 and monitor 314. In some embodiments, sensor unit 312 may be part of an oximeter. Sensor unit 312 may include one or more light source 316 for emitting light at one or more wavelengths into a subject's tissue. Detectors 318 and 338 may also be provided in sensor unit 312 for detecting the light that is reflected by or has traveled through the subject's tissue. Any suitable configuration of light source 316 and detectors 318 and 338 may be used. In some embodiments, sensor unit 312 may include multiple light sources and detectors, which may be spaced apart. In some embodiments, detector 318 (i.e., the near detector) may be positioned at a location closer to light source 316 than detector 338 (i.e., the far detector). Physiological monitoring system 310 may also include one or more additional sensor units (not shown) that may, for example, take the form of any of the embodiments described herein with reference to sensor unit 312. An additional sensor unit may be the same type of sensor unit as sensor unit 312, or a different sensor unit type than sensor unit 312 (e.g., a photoacoustic sensor). Multiple sensor units may be capable of being positioned at two different locations on a subject's body.

In some embodiments, sensor unit 312 may be connected to monitor 314 as shown. Sensor unit 312 may be powered by an internal power source, e.g., a battery (not shown). Sensor unit 312 may draw power from monitor 314. In another embodiment, the sensor may be wirelessly connected (not shown) to monitor 314. Monitor 314 may be configured to calculate physiological parameters based at least in part on data relating to light emission and acoustic detection received from one or more sensor units such as sensor unit 312. For example, monitor 314 may be configured to determine regional oxygen saturation, pulse rate, respiration rate, respiration effort, blood pressure, blood oxygen saturation (e.g., arterial, venous, or both), hemoglobin concentration (e.g., oxygenated, deoxygenated, and/or total), any other suitable physiological parameters, or any combination thereof. In some embodiments, calculations may be performed on the sensor units or an intermediate device and the result of the calculations may be passed to monitor 314. Further, monitor 314 may include display 320 configured to display the physiological parameters or other information about the system. In the embodiment shown, monitor 314 may also include a speaker 322 to provide an audible sound that may be used in various other embodiments, such as for example, sounding an audible alarm in the event that a subject's physiological parameters are not within a predefined normal range. In some embodiments, physiological monitoring system 310 may include a standalone monitor in communication with the monitor 314 via a cable or a wireless network link. In some embodiments, monitor 314 may be implemented as monitor 104 of FIG. 1.

In some embodiments, sensor unit 312 may be communicatively coupled to monitor 314 via cable 324 at port 336. Cable 324 may include electronic conductors (e.g., wires for transmitting electronic signals from detectors 318 and 338), optical fibers (e.g., multi-mode or single-mode fibers for transmitting emitted light from light source 316), any other suitable components, any suitable insulation or sheathing, or any combination thereof. In some embodiments, a wireless transmission device (not shown) or the like may be used instead of or in addition to cable 324. Monitor 314 may include a sensor interface configured to receive physiological signals from sensor unit 312, provide signals and power to sensor unit 312, or otherwise communicate with sensor unit 312. The sensor interface may include any suitable hardware, software, or both, which may allow communication between monitor 314 and sensor unit 312.

In the illustrated embodiment, physiological monitoring system 310 includes infusion pump 340. Infusion pump 340 may be communicatively coupled to monitor 314 via cable 344. In addition, infusion pump 340 may be communicatively coupled to multi-parameter physiological monitor 326 via cable 338. In some embodiments, a wireless transmission device (not shown) or the like may be used instead of or in addition to cable 344 or cable 338. Monitor 314 may include an infusion pump interface configured to receive physiological signals and data from infusion pump 340, provide signals and power to infusion pump 340, or otherwise communicate with infusion pump 340. The infusion pump interface may include any suitable hardware, software, or both, which may allow communication between monitor 314 and infusion pump 340. In some embodiments, the infusion pump interface may be configured to provide control signals to infusion pump 340 in order to cause changes in the operation of infusion pump 340. For example, infusion pump interface may generate a signal causing infusion pump 340 to alter the dosage of the drug or medication being administered to a subject by infusion pump 340. In some embodiments, infusion pump 340 may include display 342 for displaying infusion pump information, including, for example, the drug being administered, the administration dosage, any other suitable information, or any combination thereof. Display 342 may be a cathode ray tube display, a flat panel display (as shown) such as an LCD display, an LED display, a plasma display, or any other suitable display.

In some embodiments, physiological monitoring system 310 may include hospital information system 380. Hospital information system 380 may include a centralized or distributed database, data input and output terminals, primary and backup storage, or any other suitable components. Hospital information system 380 may be communicatively coupled to monitor 314 via communicative coupling 382, and/or may communicate wirelessly (not shown). Hospital information system 380 may also be communicatively coupled to multi-parameter physiological monitor 326 via communicative coupling (not shown), and/or may communicate wirelessly (not shown). In some embodiments, hospital information system 380 may include a manual input device (not shown) used by an operator to manually input clinical information obtained from some other source (e.g., an external invasive or non-invasive physiological measurement system). Hospital information system 380 may be configured to store and transmit subject data to monitor 314. In some embodiments, hospital information system 380 may be configured to store and transmit clinical information associated with a subject undergoing a clinical procedure to monitor 314. For example, hospital information system 380 may store and transmit clinical information associated with a subject undergoing a clinical procedure that affects the circulatory system of the subject.

In the illustrated embodiment, physiological monitoring system 310 includes a multi-parameter physiological monitor 326. The monitor 326 may include a cathode ray tube display, a flat panel display (as shown) such as an LCD display, an LED display, or a plasma display, or may include any other type of monitor now known or later developed. Multi-parameter physiological monitor 326 may be configured to calculate physiological parameters and to provide a display 328 for information from monitor 314 and from other medical monitoring devices or systems (not shown). For example, multi-parameter physiological monitor 326 may be configured to display an estimate of a subject's regional blood oxygen saturation generated by monitor 314. In another example, multi-parameter physiological monitor 326 may be configured to display clinical information received from infusion pump 340, hospital information system 380, and/or from other medical monitoring devices or systems (not shown). In some embodiments, multi-parameter physiological monitor 326 may be configured to determine and display status information based on the clinical information received from monitor 314, infusion pump 340, hospital information system 380, and/or from other medical monitoring devices or systems (not shown). In some embodiments, multi-parameter physiological monitor 326 may be configured to display a prompt to a user to take one or more actions as part of a smart prompt system. Multi-parameter physiological monitor 326 may include a speaker 330.

Monitor 314 may be communicatively coupled to multi-parameter physiological monitor 326 via cable 332 or 334 that is coupled to a sensor input port or a digital communications port, respectively and/or may communicate wirelessly (not shown). In addition, monitor 314 and/or multi-parameter physiological monitor 326 may be coupled to a network to enable the sharing of information with servers or other workstations (not shown). Monitor 314 may be powered by a battery (not shown) or by a conventional power source such as a wall outlet.

In some embodiments, any of the processing components and/or circuits, or portions thereof, of FIGS. 1 and 3, including sensors 102 and 312, monitors 104, 314, and 326, and pump 340 may be referred to collectively as processing equipment. For example, processing equipment may be configured to amplify, filter, sample and digitize an input signal from sensor 102 or 312 (e.g., using an analog-to-digital converter), detect changes in $rSO_2$, determine status information, and trigger action based on the status information. The processing equipment may include one or more processors. In some embodiments, all or some of the components of the processing equipment may be referred to as a processing module. In some embodiments, the processing equipment may be part of a regional oximetry system, and sensors 102 and 312 of FIGS. 1 and 3 may correspond to regional oximeter sensor unit 400 of FIG. 4.

Figure 4:
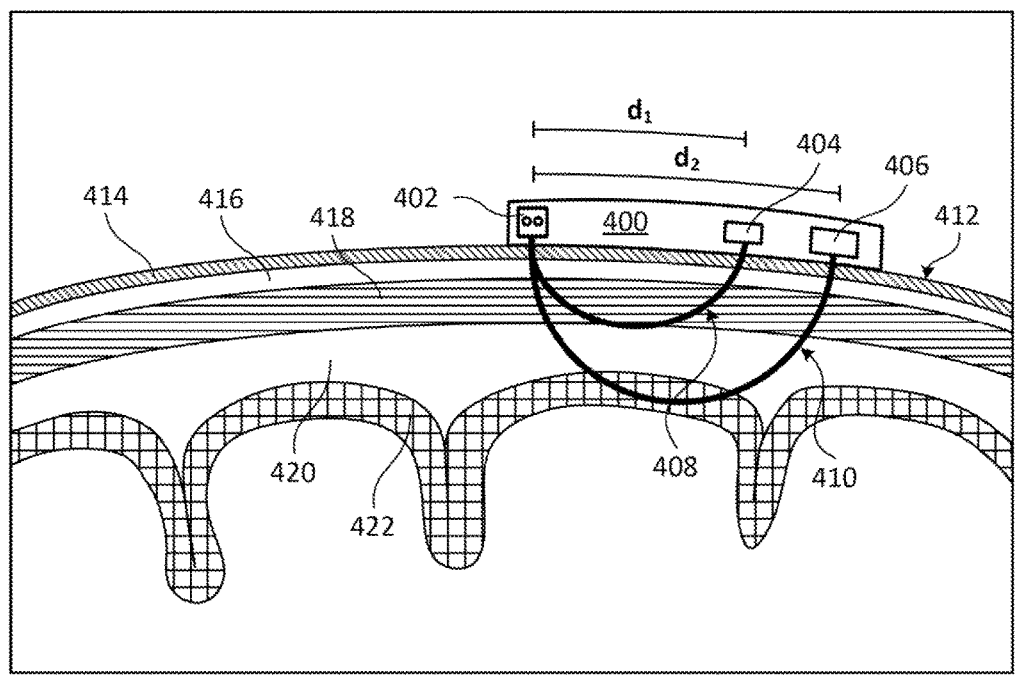
FIG. 4 is a cross-sectional view of an illustrative regional oximeter sensor unit applied to a subject's cranium in accordance with some embodiments of the present disclosure.

FIG. 4 is a cross-sectional view of an illustrative regional oximeter sensor unit 400 applied to a subject's cranium in accordance with some embodiments of the present disclosure. Regional oximeter sensor unit 400 includes light source 402, near detector 404, and far detector 406 and is shown as positioned on a subject's forehead 412. In the illustrated embodiment, light source 402 generates a light signal, which is shown traveling first and second mean path lengths 408 and 410 to respective near and far detectors 404 and 406. As shown, first and second mean path lengths 408 and 410 traverse the subject's cranial structure at different depths. The subject's cranial structure includes outer skin 414, shallow tissue 416, and cranial bone 416 (i.e., the frontal shell of the skull). Beneath cranial bone 416 is Dura Mater 420 and cerebral tissue 422.

In some embodiments, light source 402 of sensor unit 400 may include one or more emitters for emitting light into the tissue of a subject to generate physiological signals. Detectors 404 and 406 may be positioned on sensor unit 400 such that near detector 404 is located at a distance $d_1$ from light source 402 and far detector 406 is located at a distance $d_2$ from light source 402. As shown, distance $d_1$ is shorter than distance $d_2$, and it will be understood that any suitable distances $d_1$ and $d_2$ may be used such that mean path length 408 of light detected by near detector 404 is shorter than the mean path length 410 of far detector 406. Near detector 404 may receive the light signal after it has traveled first mean path length 408, and far detector 406 may receive the light signal after it has traveled second mean path length 410. First mean path length 408 may traverse the subject's outer skin 414, shallow tissue 416, cranial bone 416, and Dura Mater 420. In some embodiments, first mean path length 408 may also traverse shallow cerebral tissue 422. Second mean path length 410 may traverse the subject's outer skin 414, shallow tissue 416, cranial bone 416, Dura Mater 420, and cerebral tissue 422.

In some embodiments, regional oximeter sensor unit 400 may be part of a regional oximetry system for determining the amount of light absorbed by a region of a subject's tissue. As described in detail above, for each wavelength of light, an absorption value may be determined based on the amount of light received at near detector 404, and an absorption value may be determined based on the amount of light received at far detector 406. For each wavelength of light, a differential absorption value may be computed based on the difference between the absorption values determined for near detector 404 and far detector 406. The differential absorption values may be representative of the amount of light absorbed by cerebral tissue 422 at each wavelength. In some embodiments, the differential absorption values $\Delta A_{\lambda,i}$ may be given by:

$$\Delta A_{\lambda,i} = A_{\lambda,i,shall} - A_{\lambda,i,deep}, \quad (1)$$

where $A_{\lambda,i,deep}$ denotes the attenuation of light between light source 402 and far detector 406, $A_{\lambda,i,shall}$ denotes the attenuation of light between light source 402 and near detector 404, and $\lambda_i$ denotes a wavelength of light. In some embodiments, a detected light signal may be normalized, for example, based on the amount of light emitted by light source 402, characteristics of the detector, system gains, other suitable properties of the system, and/or empirical data. The processing equipment may determine the differential absorption values $\Delta A_{\lambda,i}$ based on eq. 1, using normalized values for the attenuation of light between light source 402 and far detector 406 and the attenuation of light between light source 402 and near detector 404. Using known methods, the processing equipment may determine an $rSO_2$ value for a region of the subject's tissue based on the differential absorption values. In the illustrated embodiment, an $rSO_2$ value may be determined for a region of the subject's cerebral tissue 422. It will be understood that while the foregoing techniques for determining $rSO_2$ were described with reference to cerebral tissue, $rSO_2$ may be calculated for any suitable region of a subject's tissue.

As described above, $rSO_2$ is a measure of the oxygen saturation of blood in a region of the subject's tissue (e.g., cerebral tissue 422), which may include blood in the venous, arterial, and capillary systems. Accordingly, a change in an $rSO_2$ value of a subject may be indicative of a change in the subject's circulatory system (i.e., blood distribution network, including the heart, blood, and blood vessels). Certain clinical procedures carry with them an elevated risk of impairing the functionality of the subject's circulatory system. The processing equipment may monitor a subject undergoing a clinical procedure by detecting changes in the $rSO_2$ of a subject, which may be indicative of circulatory distress caused by the clinical procedure.

Figure 5:
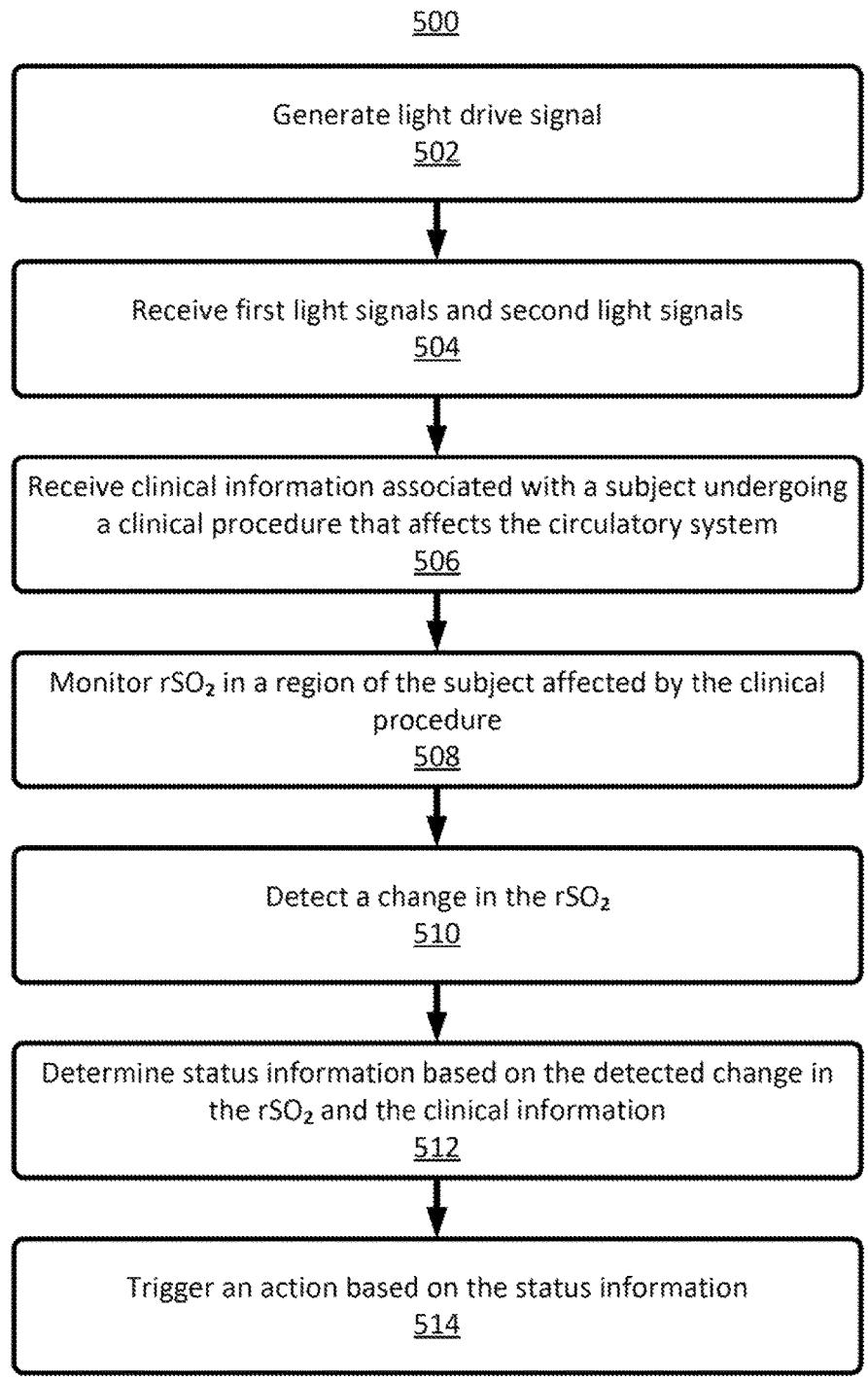
FIG. 5 shows an illustrative flow diagram including steps for monitoring a clinical procedure using $rSO_2$ in accordance with some embodiments of the present disclosure.

FIG. 5 shows an illustrative flow diagram 500 including steps for monitoring a clinical procedure using $rSO_2$ in accordance with some embodiments of the present disclosure.

At step 502, the processing equipment may generate a light drive signal configured to cause one or more light sources to emit light signals corresponding to wavelengths of light. The one or more light sources may correspond to light source 130 of FIG. 1, 316 of FIG. 3, or 402 of FIG. 4. The light drive signal may correspond to the light drive signal shown in FIG. 2A.

At step 504, the processing equipment may receive first light signals corresponding to wavelengths of light that have been attenuated by a first region of a subject and second light signals corresponding to wavelengths of light that have been attenuated by a second region of the subject. First light signals may travel first mean path length 408 of FIG. 4. Second light signals may travel second mean path length 410 of FIG. 4. In some embodiments, the first signals may be received by a near detector, which may correspond to near detector 404 of FIG. 4, and the second signals may be received by a far detector, which may correspond to far detector 406 of FIG. 4. As described above, the first region may correspond to a smaller, shallow region of tissue than the second region, which may correspond to a larger, deep region of tissue. For example, the processing equipment may be implemented as part of a cerebral oximeter, where the first region may include the subject's outer skin, shallow tissue, cranial bone, Dura Mater, and shallow cerebral tissue, and the second region may include all of the first region and the subject's deeper cerebral tissue.

At step 506, the processing equipment may receive clinical information associated with a subject undergoing a clinical procedure that affects the circulatory system (e.g., a clinical procedure that occludes a blood vessel). It will be understood that clinical information may be received for any suitable clinical procedure. In some embodiments, the clinical information may include information that a subject is presently undergoing a clinical procedure. In some embodiments, the clinical information may include information that a subject is scheduled to undergo a clinical procedure at a future time. In some embodiments, clinical information may include, for example, the type of clinical procedure, drug and dosage information for drugs administered as part of the clinical procedure, known risks associated with the clinical procedure, any effect the clinical procedure may have on a subject's circulatory system, technical specifications for any device being used in performing the clinical procedure, any other suitable clinical information associated with the subject undergoing a clinical procedure, or any combination thereof. In some embodiments, a monitor such as monitor 314 or multi-parameter physiological monitor 326 of FIG. 3 may receive the clinical information. In some embodiments, processing equipment such as back end processing circuitry 170 of FIG. 1 may receive the clinical information. In some embodiments, the processing equipment may receive clinical information from user input, for example, user input 182 of FIG. 1. In some embodiments, the processing equipment may receive clinical information from a hospital information system, for example, hospital information system 380 of FIG. 3. In some embodiments, the processing equipment may receive clinical information from an infusion pump, for example, infusion pump 340 of FIG. 1. In some embodiments, the processing equipment may receive clinical information from any suitable external device or system associated with the respective clinical procedure. In some embodiments, the processing equipment may store the received clinical information in memory, for example, memory 174 of FIG. 1.

At step 508, the processing equipment may monitor $rSO_2$ in a region of the subject affected by the clinical procedure based on first received light signals and second received light signals. For example, the processing equipment may monitor the $rSO_2$ in a region of the subject based on the first and second pluralities of light signals received in step 504. In some embodiments, a regional oximetry sensor unit, such as sensor 102 of FIG. 1, sensor unit 312 of FIG. 3, or regional oximetry sensor unit 400 of FIG. 4, may be positioned on the subject above a region of tissue that may be affected by the clinical procedure. For example, for a clinical procedure involving occluding an artery of a subject, a regional oximetry sensor unit may be positioned on the subject, downstream relative to the blood flow of the occluded artery, such that the processing equipment may monitor the $rSO_2$ of a region affected by the clinical procedure. In some embodiments, the processing equipment may monitor $rSO_2$ in one or more regions of the subject affected by the clinical procedure (e.g., using one or more regional oximetry sensor units).

At step 510, the processing equipment may detect a change in the $rSO_2$ of the subject. In some embodiments, the processing equipment may detect one or more changes in the rSO$_2$ of the subject. In some embodiments, a detected change in the rSO$_2$ of a subject may be indicative of a change in the subject's circulatory system. For example, a detected change in the rSO$_2$ of a subject may be indicative of a change in venous oxygen saturation, as described below with reference to FIG. 6, or a change in tissue perfusion, as described below with reference to FIGS. 7 and 8. In some embodiments, the processing equipment may compare a detected change to a predetermined threshold to determine whether the change is a significant change. For example, if the change in rSO$_2$ falls below a predetermined threshold, the processing equipment may determine it is a significant change. In some embodiments, the predetermined threshold is adjustable based on user input, for example user input 182 of FIG. 1. In some embodiments, the predetermined threshold is adjustable based on clinical information. In some embodiments, detecting a change in step 510 may include detecting when the rSO$_2$ crosses a threshold, determining the slope of the rSO$_2$, detecting a pattern of changes in rSO$_2$, detecting any other behavior of the rSO$_2$, and any combination thereof.

At step 512, the processing equipment may determine status information based on the detected change in the rSO$_2$ and the received clinical information. In some embodiments, the processing equipment may determine status information only if the detected change in the rSO$_2$ is a significant change (e.g., exceeds a predetermined threshold), as described above in step 510. In some embodiments, the status information may be indicative of an increased risk of a physiological event (e.g., a blood clot). Physiological event, as used herein, may refer to any adverse physiological event associated with a clinical procedure that affects the circulatory system or any other suitable clinical procedure. For example, an increased risk of a physiological event may be the result of a circulatory system impairment caused by a clinical procedure. In some embodiments, the detected change in the rSO$_2$ may be indicative of an effect on the circulatory system caused by a clinical procedure, and the status information may be indicative of an increased risk of a physiological event associated with the effect on the circulatory system. For example, the processing equipment may receive clinical information associated with the subject undergoing a clinical procedure involving occlusion of an artery of a subject, and the processing equipment may detect a change in the rSO$_2$ of a region of the subject's tissue affected by the clinical procedure. The processing equipment may determine status information that is indicative of an increased risk of embolism (e.g., blood clot) based on the detected change in the rSO$_2$ and the received clinical information that the subject was undergoing the clinical procedure, which carries with it a risk of embolism.

At step 514, the processing equipment may trigger an action based on the determined status information. In some embodiments, the processing equipment may output an alert signal indicative of the increased risk. For example, the processing equipment may display a warning message on display 184 of FIG. 1 or display 320 of FIG. 3. In some embodiments, the processing equipment may output an alert sound, for example, using speaker 186 of FIG. 1, or speaker 322 of monitor 314 or speaker 330 of multi-parameter physiological monitor 326 of FIG. 3. In some embodiments, the processing equipment may display the status information. In some embodiments, the processing equipment may prompt one or more corrective actions for reducing the increased risk of a physiological event. For example, the processing equipment may implemented as a smart prompt system for prompting the user to perform the one or more corrective actions. In some embodiments, the one or more corrective actions may be displayed, for example, using display 184 of FIG. 1 or display 320 of FIG. 3. In some embodiments, the processing equipment may select at least one of the one or more displayed corrective actions based on user input, for example, user input 182 of FIG. 1. In some embodiments, the processing equipment may perform the at least one selected corrective action. In some embodiments, the processing equipment may automatically perform one or more corrective actions for reducing the risk of a physiological event. In some embodiments, the status information may be indicative of a severity of the increased risk, and the processing equipment may select at least one of the one or more corrective actions based on the severity of the increased risk and automatically perform the at least one selected corrective action. In some embodiments, the processing equipment may implement a closed loop system for controlling a clinical procedure based on a detected change in the rSO$_2$. In some embodiments, a monitor such as monitor 314 or multi-parameter physiological monitor 326 of FIG. 3 may automatically trigger an action based on the status information. In some embodiments, processing equipment such as back end processing circuitry 170 of FIG. 1 may trigger an action based on the status information. In some embodiments, the processing equipment may trigger an action by outputting a signal to an external device or system associated with the clinical procedure. For example, the processing equipment may generate a signal that is provided to an infusion pump, for example, infusion pump 340 of FIG. 3, and the signal may control the particular drug or medicine to be administered to the subject by infusion pump 340.

In some embodiments, the processing equipment may detect an updated change in the rSO$_2$ of the subject based on the one or more corrective actions. For example, once the processing equipment or the user has performed a corrective action, the processing equipment may determine an updated change in the rSO$_2$, as described in step 510. In some embodiments, the processing equipment may update the status information based on the previously determined status information, the clinical information, and the updated change in the rSO$_2$ of the subject. For example, the processing equipment may detect an updated change in the rSO$_2$ of the subject, which indicates the rSO$_2$ is decreasing. The processing equipment may determine updated status information indicative of a decreased risk of a physiological event (relative to the previously determined status information) based on the indication of decreasing rSO$_2$, the clinical information, and the previously determined status information. In some embodiments, the processing equipment may display the updated status information, using, for example, display 184 of FIG. 1 or display 320 of FIG. 3. For example, the displayed status information may provide the user with an indication of the effectiveness of the one or more corrective actions that have been performed.

It will be understood that the steps above are exemplary and that in some implementations, steps may be added, removed, omitted, repeated, reordered, modified in any other suitable way, or any combination thereof.

Figure 6:
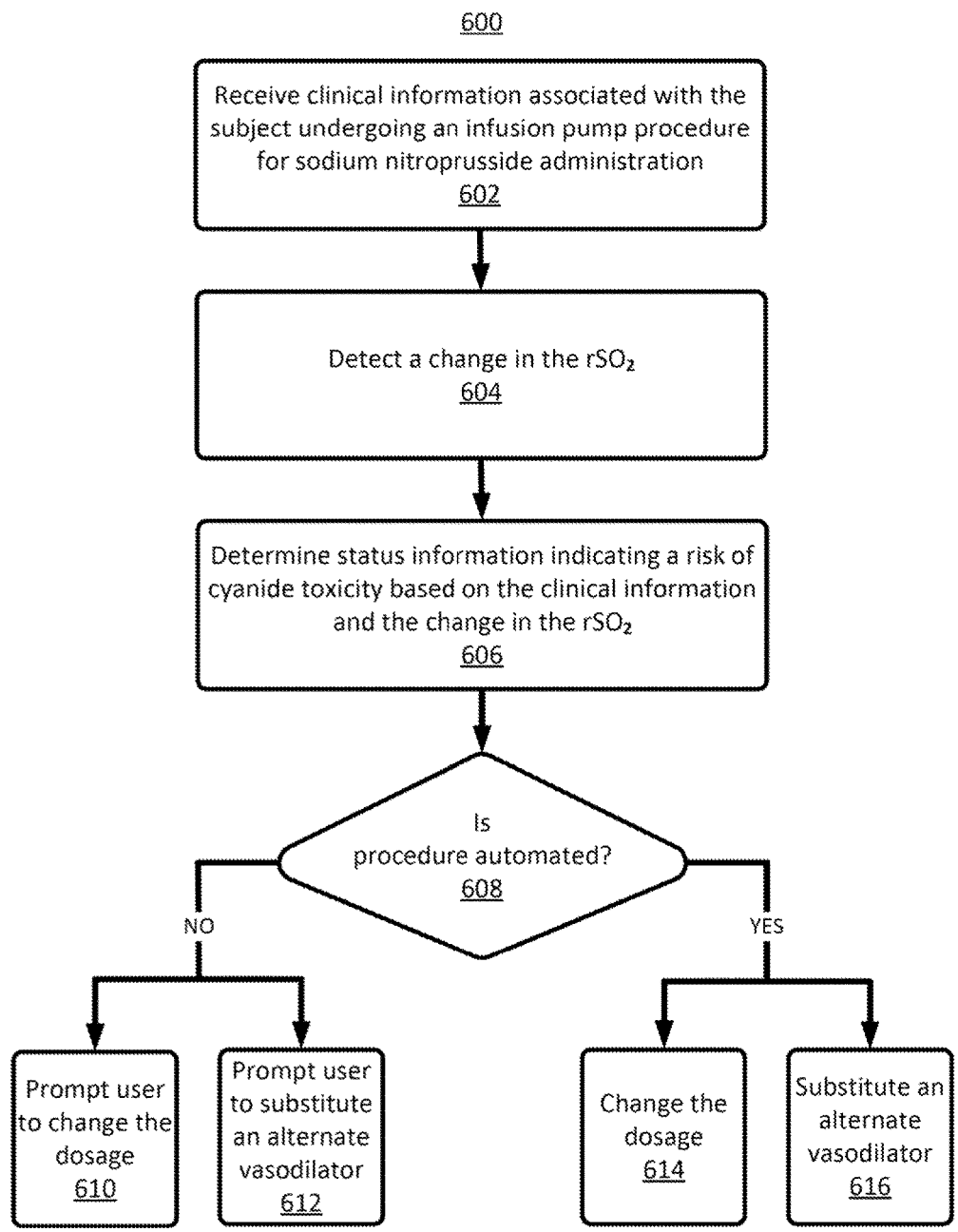
FIG. 6 shows an illustrative flow diagram including steps for monitoring an infusion pump procedure for nitroprusside administration using $rSO_2$ in accordance with some embodiments of the present disclosure.
Figure 7:
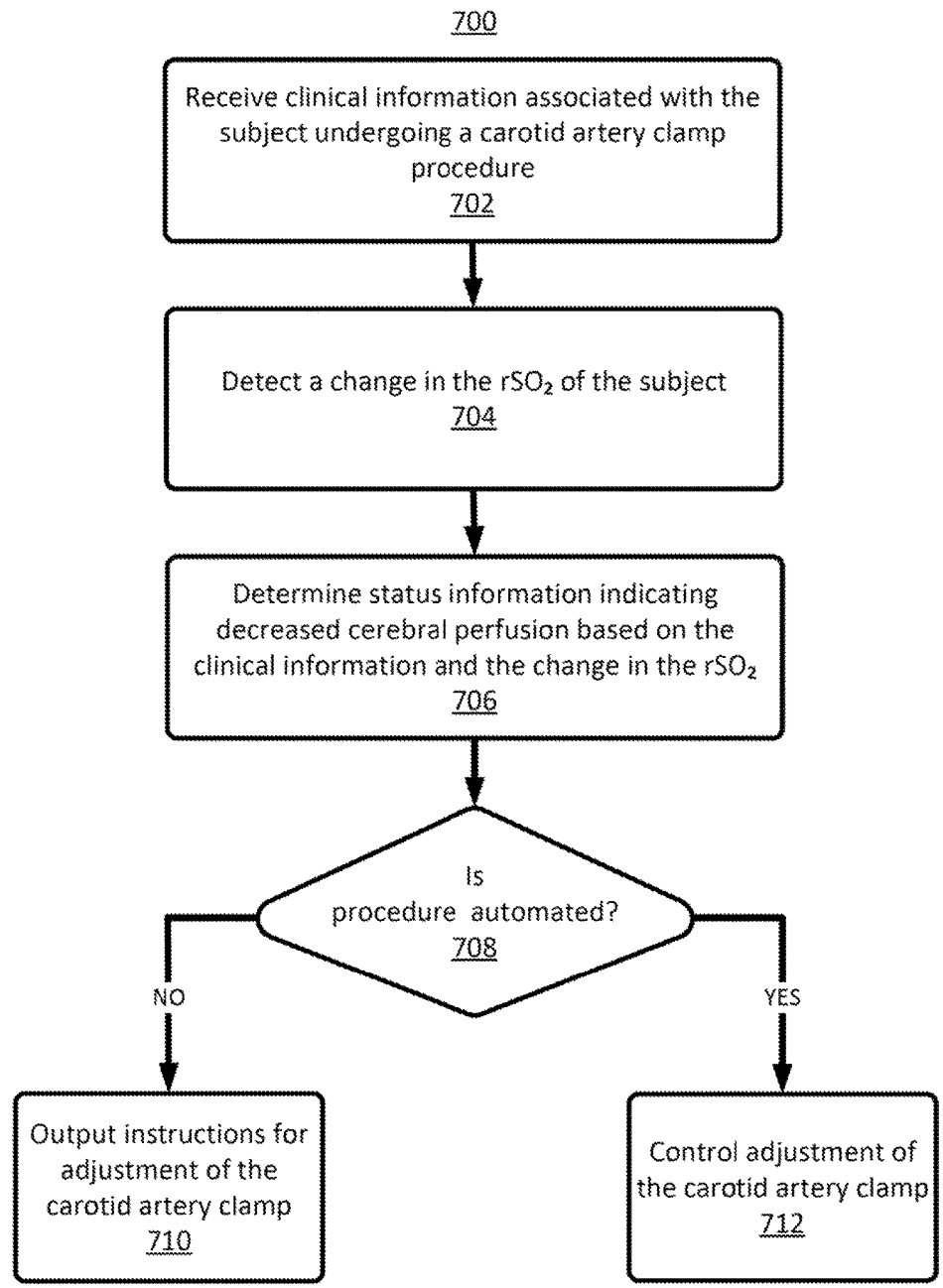
FIG. 7 shows an illustrative flow diagram including steps for monitoring a carotid artery clamp procedure using $rSO_2$ in accordance with some embodiments of the present disclosure.
Figure 8:
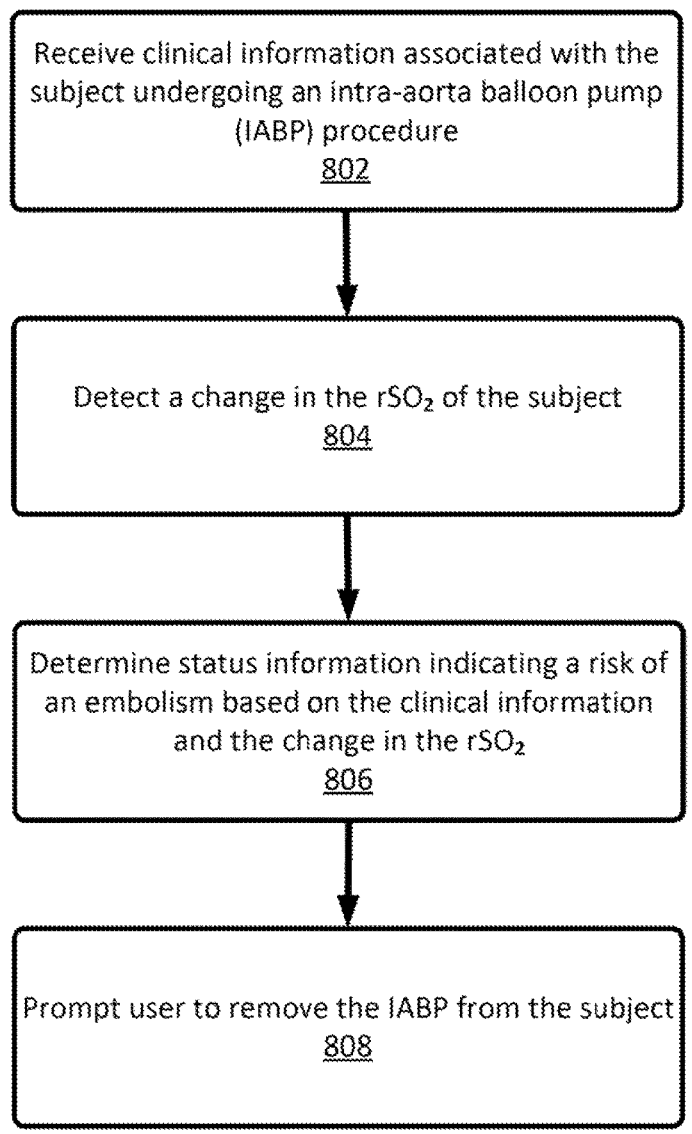
FIG. 8 shows an illustrative flow diagram including steps for monitoring an intra-aorta balloon pump procedure using $rSO_2$ in accordance with some embodiments of the present disclosure.

Some embodiments of FIG. 5 are further discussed with reference to FIGS. 6-8. As noted above, a change in an rSO$_2$ value of a subject may be indicative of a change in the subject's circulatory system (i.e., blood distribution network, including the heart, blood, and blood vessels). Certain clinical procedures carry with them an elevated risk of impairing the functionality of the subject's circulatory system. The processing equipment may monitor a subject undergoing a clinical procedure by detecting changes in the $rSO_2$ of a subject, which may be indicative of circulatory system impairment (i.e., elevated venous oxygen saturation and/or decreased tissue perfusion) caused by the clinical procedure. FIGS. 6-8 show illustrative flow diagrams for monitoring specific clinical procedures using $rSO_2$ in accordance with some embodiments of the present disclosure.

A change in the $rSO_2$ of a subject may be indicative of a change in the venous oxygen saturation of a subject. Certain clinical procedures may be associated with a risk of elevated venous oxygen saturation, including, for example, an infusion pump procedure for administration of sodium nitroprusside (i.e., a vasodilator). An infusion pump, such as infusion pump 340 of FIG. 3, may be used to intravenously administer sodium nitroprusside to a subject. For example, a subject with systemic hypertension may be treated with intravenous sodium nitroprusside. When hemoglobin in the blood metabolizes sodium nitroprusside, cyanide is produced as a byproduct. Cyanide production can result in cyanide toxicity. One symptom of cyanide poisoning is reduced tissue oxygen utilization, which can lead to elevated venous oxygen saturation. Accordingly, cyanide toxicity may be quickly detected and corrected by monitoring the $rSO_2$ of a subject for indications of elevated venous oxygen saturation occurring while the subject is receiving intravenous sodium nitroprusside. In some embodiments, the processing equipment may monitor a subject undergoing a an infusion pump procedure for nitroprusside administration by detecting a change in the $rSO_2$ of a subject, which may be indicative of elevated venous oxygen saturation caused by the procedure, as shown in FIG. 6.

FIG. 6 shows an illustrative flow diagram 600 including steps for monitoring an infusion pump procedure for sodium nitroprusside administration using $rSO_2$ in accordance with some embodiments of the present disclosure. In some embodiments, the processing equipment may perform steps 502 and 504 of FIG. 5, as described above, before performing step 602.

At step 602, the processing equipment may receive clinical information associated with a subject undergoing an infusion pump procedure for sodium nitroprusside administration. In some embodiments, step 602 may correspond to step 506 of FIG. 5. As described above, in some embodiments, the clinical information may be received from an infusion pump, for example, infusion pump 340 of FIG. 3. In some embodiments, clinical information may include information indicating that a subject is or will be undergoing an infusion pump procedure for sodium nitroprusside administration, technical details of the infusion pump (e.g., automated or non-automated system, capacity for administering more than one drug), the type and dose of drug being administered (i.e., sodium nitroprusside), the risk of cyanide toxicity associated with sodium nitroprusside administration, the symptoms of cyanide toxicity (e.g., elevated venous oxygen saturation), information about the subject undergoing the procedure, any other suitable clinical information, or any combination thereof.

At step 604, the processing equipment may detect a change in the $rSO_2$ of a subject. In some embodiments, detecting a change in the $rSO_2$ of the subject may correspond to step 510 of FIG. 5. In some embodiments, detecting a change in the $rSO_2$ of the subject may correspond to steps 508 and 510 of FIG. 5. In some embodiments, the processing equipment may detect a change in the $rSO_2$ in a region of the subject affected by the infusion pump procedure. For example, the processing equipment may determine the $rSO_2$ in a localized region of tissue around or, with respect to blood flow, downstream of the infusion pump, for example, infusion pump 340 of FIG. 3.

In some embodiments, the processing equipment may detect a change in the $rSO_2$ of a subject that may be indicative of a change in the venous oxygen saturation of a subject. Because regional pulse oximetry monitors the blood in the arterial and venous systems in a region of tissue, $rSO_2$ is a measure based on the combination of arterial oxygen saturation ($S_aO_2$) and venous oxygen saturation ($S_vO_2$). In some embodiments, the processing equipment may estimate a subject's venous oxygen saturation based on the subject's regional oxygen saturation, arterial oxygen saturation, and the ratio of arterial and venous blood in the region of tissue for which the $rSO_2$ is being measured. As described above, the present disclosure may be implemented in a combined oximeter, which includes both a regional oximeter and a pulse oximeter, and thus, the processing equipment may determine an $rSO_2$ value and an $S_aO_2$ value for the subject. The processing equipment may estimate what portion of the blood passing through a region of tissue corresponds to venous blood and what portion corresponds to arterial blood. For example, ⅓ may be arterial blood and ⅔ may be venous blood. After determining the $rSO_2$ and $S_aO_2$ of a region of tissue and the venous/arterial composition of the blood in the region of tissue, the processing equipment may determine the $S_vO_2$ based on the following relationship:

$$rSO_2 = (x)S_aO_2 + (y)S_vO_2, \qquad (2)$$

where x denotes the fraction of blood in the region of tissue corresponding to arterial blood, y denotes the fraction of blood in the region of tissue corresponding to venous blood, and $x+y=1$. In an example, the processing equipment may compute an $rSO_2$ value of 73% and an $S_aO_2$ value of 95% and may determine that ⅓ of the blood in the region is arterial blood (x=⅓) and ⅔ is venous blood (y=⅔). Using Eq. 2 and these exemplary input values, the processing equipment may determine an estimated $S_vO_2$ value of 62%. In another example, if the $S_vO_2$ value of the subject were elevated to 85%, then, assuming all else equal, the processing equipment may determine an $rSO_2$ value of approximately 88%. Because regional oximetry typically examines regions of tissue composed mostly of venous blood, a detected change in the $rSO_2$ value may serve as an indicator of a change in the $S_vO_2$ value. In some embodiments, the processing equipment may compute a change in $S_vO_2$ based on a detected change in $rSO_2$. In some embodiments, the processing equipment may infer, based on the detected change in $rSO_2$, that the $S_vO_2$ has also changed. For example, a detected increase in $rSO_2$ may indicate an increase in $S_v O_2$. In some embodiments, the processing equipment may compare a detected change in $rSO_2$ to a predetermined threshold to determine whether the change is a significant change. The processing equipment may determine there has been a change in $S_vO_2$ if the detected change is a significant change. For example, if the $rSO_2$ exceeds a predetermined threshold, the processing equipment may determine it is a significant change. In some embodiments, the processing equipment may infer that a detected change in $rSO_2$ is indicative of a change in $S_vO_2$ only if the detected change in $rSO_2$ is a significant change.

At step 606, the processing equipment may determine status information indicating an increased risk of cyanide toxicity based on the clinical information and the detected change in the $rSO_2$ of a subject. In some embodiments, the processing equipment may determine status information only if the detected change in the $rSO_2$ is a significant change (i.e., exceeds a predetermined threshold), as described above in step 510. In some embodiments, the status information may be indicative of an increased risk of cyanide toxicity, and the processing equipment may determine the status information based on a detected increase in the $rSO_2$. In some embodiments, the processing equipment may determine status information based on the clinical information and an indication of elevated $S_vO_2$, which may be computed or inferred based on a detected increase in the $rSO_2$ as described above in step 604. In some embodiments, step 606 may correspond to step 512 of FIG. 5.

At step 608, if the procedure is not automated, the processing equipment will proceed to steps 610 and 612. If the procedure is automated, the processing equipment will proceed to steps 614 and 616. In some embodiments, the processing equipment may determine if the procedure is automated or not automated.

If the infusion pump procedure is not automated, the processing equipment may prompt the user to perform one or more corrective actions for reducing the risk of cyanide toxicity, as described above with reference to step 514 of FIG. 5. At step 610, the processing equipment may prompt the user to change the dosage of sodium nitroprusside being administered. The processing equipment may provide the user with one or more suggested dose changes based on received clinical information indicating the current dosage and the status information. In some embodiments, prompting a dose change may include prompting a reduction in the infusion rate of the infusion pump procedure. At step 612, the processing may additionally or alternatively prompt the user to terminate sodium nitroprusside administration and to substitute an alternate vasodilator. In some embodiments, the status information may be indicative of a severity of the risk of cyanide toxicity. The processing equipment may determine, based on the severity of the risk of cyanide toxicity information, whether to prompt a dose change (step 610) or substitution of a different vasodilator (step 612). In some embodiments, the corrective action to be performed may be selected based on user input, for example, user input 182 of FIG. 1, and the processing equipment may perform the selected corrective action.

If the infusion pump procedure is automatic, the processing equipment may automatically perform one or more corrective actions for reducing the risk of cyanide toxicity, as described above with reference to step 514 of FIG. 5. In some embodiments, the processing equipment may be part of a closed loop system for adjusting the infusion pump procedure based on the status information. At step 614, the processing system may automatically change the dosage of sodium nitroprusside being administered to the subject based on the status information. In some embodiments, automatically changing the dosage may include reducing the infusion rate. At step 616, the processing system may automatically terminate sodium nitroprusside administration and substitute an alternate vasodilator based on the status information. The processing equipment may determine, based on the severity of the risk of cyanide toxicity whether to change the dosage (step 614) or substitute a different vasodilator (step 616).

As described above with reference to step 514 of FIG. 5, in some embodiments, the processing equipment may detect an updated change in the $rSO_2$ of the subject based on the one or more corrective actions, and the processing equipment may update the status information based on the previously determined status information, the clinical information, and the updated change in the $rSO_2$ of the subject. For example, the processing equipment may detect an updated change in the $rSO_2$ of the subject, which indicates the $rSO_2$ is decreasing. The processing equipment may determine updated status information indicative of a decreased risk of a cyanide toxicity (relative to the previously determined increased risk of cyanide toxicity) based on the indication of decreasing $rSO_2$, which may be indicative of decreasing $S_vO_2$, the clinical information, and the previously determined status information. In some embodiments, the processing equipment may display the updated status information, using, for example, display 184 of FIG. 1 or display 320 of FIG. 3.

In addition to providing an indication of $S_vO_2$, as described above, with reference to FIG. 6, a change in the $rSO_2$ of a subject may be indicative of a change in the tissue perfusion of the region of tissue being analyzed. As described above, a subject's $rSO_2$ is representative of the oxygen saturation of blood in a region of the subject's tissue which may include blood in the venous, arterial, and capillary systems. Thus, a change in $rSO_2$ for a region of a subject's tissue may be indicative of a change in tissue perfusion. As used herein, tissue perfusion refers, generally, to the volume of blood flowing through arteries and capillaries in a region of tissue of a subject, delivering oxygen to that region of tissue. Impaired tissue perfusion may be caused by vascular occlusion (i.e., blockage in a blood vessel). Certain clinical procedures may be associated with a risk of decreased tissue perfusion. In some embodiments, the processing equipment may monitor a subject undergoing a clinical procedure (e.g., a carotid artery clamp or intra-aorta balloon pump procedure) by detecting a change in the $rSO_2$ of a subject, which may be indicative of a change in tissue perfusion caused by the clinical procedure, as shown in FIGS. 7 and 8.

FIG. 7 shows an illustrative flow diagram 700 including steps for monitoring a carotid artery clamp procedure using $rSO_2$ in accordance with some embodiments of the present disclosure. A carotid artery clamp procedure involves a gradual closing of a surgically implanted carotid artery clamp, which is associated with a risk of decreased cerebral perfusion (e.g., stroke). In some embodiments, the processing equipment may perform steps 502 and 504 of FIG. 5, as described above, before performing step 702.

At step 702, the processing equipment may receive clinical information associated with the subject undergoing a carotid artery clamp procedure. In some embodiments, step 702 may correspond to step 506 of FIG. 5. The processing equipment may receive the clinical information from any suitable source, including, but not limited to, a carotid artery clamp system. In some embodiments, clinical information may include information indicating that a subject is or will be undergoing a carotid artery clamp procedure, technical details of the carotid artery clamp (e.g., automated or non-automated system, adjustment mechanism details), the risk of stroke associated with the procedure, the symptoms or causal factors of a stroke associated with the procedure (e.g., decreased cerebral perfusion), any other suitable clinical information, or any combination thereof.

At step 704, the processing equipment may detect a change in the $rSO_2$ of a subject. In some embodiments, detecting a change in the $rSO_2$ of the subject may correspond to step 510 of FIG. 5. In some embodiments, detecting a change in the $rSO_2$ of the subject may correspond to steps 508 and 510 of FIG. 5. In some embodiments, the processing equipment may detect a change in the $rSO_2$ in a region of the subject affected by the carotid artery clamp procedure. For example, the processing equipment may detect a change in $rSO_2$ of a region of cerebral tissue (i.e., cerebral $rSO_2$) that may be affected by the procedure. In some embodiments, the processing equipment may detect a change in cerebral $rSO_2$ of a subject that is indicative of a change in cerebral perfusion, as described above. In some embodiments, the processing equipment may compare a detected change in cerebral $rSO_2$ to a predetermined threshold to determine whether the change is a significant change, as described above in step 510.

At step 706, the processing equipment may determine status information indicating an increased risk of decreased cerebral perfusion based on the clinical information and the detected change in the $rSO_2$ of a subject. In some embodiments, the processing equipment may determine status information only if the detected change in the $rSO_2$ is a significant change (i.e., exceeds a predetermined threshold), as described above in step 510. In some embodiments, the status information may be indicative of an increased risk of decreased cerebral perfusion, and the processing equipment may determine the status information based on a detected decrease in the $rSO_2$. In some embodiments, step 706 may correspond to step 512 of FIG. 5.

At step 708, if the procedure is not automated, the processing equipment will proceed to step 710. If the procedure is automated, the processing equipment will proceed to step 712. In some embodiments, the processing equipment may determine if the procedure is automated or not automated.

If the carotid artery clamp procedure is not automated, the processing equipment may prompt the user to perform one or more corrective actions for reducing the risk of decreased cerebral perfusion, as described above with reference to step 514 of FIG. 5. At step 710, the processing equipment may output instructions for adjustment of the carotid artery clamp. In some embodiments, instructions for adjustment of the carotid artery clamp may include the rate at which the clamp is to be closed (e.g., when to adjust the clamp and by how much). In some embodiments, the processing equipment may adjust the carotid artery clamp based on user input, for example, user input 182 of FIG. 1. In some embodiments, the status information may be indicative of a severity of the risk of decreased cerebral perfusion. The processing equipment may determine, based on the severity of the risk of decreased cerebral perfusion, what instructions to output for adjustment of the carotid artery clamp (e.g., what rate the clamp should be closed at, whether to maintain the current clamp position, whether to open the clamp, etc.). In some embodiments, the manner in which the clamp should be adjusted (i.e., the instructions for adjustment) may be selected based on user input, for example, user input 182 of FIG. 1, and the processing equipment may perform the selected adjustment of the carotid artery clamp.

If the carotid artery clamp procedure is automatic, the processing equipment may automatically perform one or more corrective actions for reducing the risk of decreased cerebral perfusion, as described above with reference to step 514 of FIG. 5. In some embodiments, the processing equipment may be part of a closed loop system for adjusting the carotid artery clamp based on the status information. At step 712, the processing equipment may automatically control the adjustment of the carotid artery clamp based on the status information. The processing equipment may determine, based on the severity of the risk of decreased cerebral perfusion, at what rate to adjust the carotid artery clamp.

As described above with reference to step 514 of FIG. 5, in some embodiments, the processing equipment may detect an updated change in the $rSO_2$ of the subject based on the one or more corrective actions, and the processing equipment may update the status information based on the previously determined status information, the clinical information, and the updated change in the $rSO_2$ of the subject. For example, the processing equipment may detect an updated change in the $rSO_2$ of the subject, which indicates the $rSO_2$ is increasing. The processing equipment may determine updated status information indicative of a decreased risk of decreased cerebral perfusion (relative to the previously determined increased risk of decreased cerebral perfusion) based on the indication of increasing $rSO_2$, which may be indicative of increasing cerebral perfusion, the clinical information, and the previously determined status information. In some embodiments, the processing equipment may display the updated status information, using, for example, display 184 of FIG. 1 or display 320 of FIG. 3. In some embodiments, the processing equipment may update the status information after each adjustment of the carotid artery clamp so as to provide the user with an indication of the results of the adjustment. In some embodiments, the processing equipment may update the instructions output to the user for adjusting the carotid artery clamp based on the updated status information, and as a result, the user may be able to close the clamp relatively rapidly, while maintaining a low risk of stroke.

FIG. 8 shows an illustrative flow diagram 800 including steps for monitoring an intra-aorta balloon pump (IABP) procedure using $rSO_2$ in accordance with some embodiments of the present disclosure. An IABP procedure involves the surgical insertion of a balloon-tipped catheter into the femoral artery of a subject's leg and is associated with a risk of embolism in the leg below the cannulated femoral artery. An embolism may cause decreased tissue perfusion. In some embodiments, the processing equipment may perform steps 502 and 504 of FIG. 5, as described above, before performing step 802.

At step 802, the processing equipment may receive clinical information associated with the subject undergoing an intra-aorta balloon pump (IABP) procedure.

In some embodiments, step 802 may correspond to step 506 of FIG. 5. The processing equipment may receive the clinical information from any suitable source, including, but not limited to, user input or an IAPB system. In some embodiments, clinical information may include information indicating that a subject is or will be undergoing an IAPB procedure, technical details of the IAPB procedure, the risk of embolism associated with the procedure, the symptoms or causal factors of an embolism associated with the procedure (e.g., decreased tissue perfusion), any other suitable clinical information, or any combination thereof.

At step 804, the processing equipment may detect a change in the $rSO_2$ of the subject.

In some embodiments, detecting a change in the $rSO_2$ of the subject may correspond to step 510 of FIG. 5. In some embodiments, detecting a change in the $rSO_2$ of the subject may correspond to steps 508 and 510 of FIG. 5. In some embodiments, the processing equipment may detect a change in the $rSO_2$ in a region of the subject affected by the IABP procedure. In some embodiments, the IABP procedure may involve cannulating an artery in the leg of a subject (e.g., the femoral artery), and the processing equipment may detect a change in the $rSO_2$ of a region of leg tissue, where the region is distal to the location at which the artery was cannulated. For example, the processing equipment may detect a change in $rSO_2$ of a region of lower leg tissue that is below the location at which the IABP was inserted. In some embodiments, the processing equipment may detect a change in $rSO_2$ of a subject that is indicative of a change in tissue perfusion, as described above. In some embodiments, the processing equipment may compare a detected change in tissue $rSO_2$ to a predetermined threshold to determine whether the change is a significant change, as described above in step 510.

At step 806, the processing equipment may determine status information indicating an increased risk of an embolism based on the clinical information and the detected change in the $rSO_2$ of a subject. In some embodiments, the processing equipment may determine status information only if the detected change in the $rSO_2$ is a significant change (i.e., exceeds a predetermined threshold), as described above in step 510. In some embodiments, the status information may be indicative of an increased risk of decreased tissue perfusion, and the processing equipment may determine the status information based on a detected decrease in the $rSO_2$. In some embodiments, step 706 may correspond to step 512 of FIG. 5.

In some embodiments, the processing equipment may prompt the user to perform one or more corrective actions for reducing the risk of decreased tissue perfusion, as described above with reference to step 514 of FIG. 5. At step 808, the processing equipment may prompt the user to remove the IABP from the subject. At step 808, the processing equipment may prompt the user to remove the IABP from the subject and re-insert the IABP at a different location on the subject. In some embodiments, the status information may be indicative of a severity of the risk of decreased cerebral perfusion. The processing equipment may determine, based on the severity of the risk of decreased cerebral perfusion, whether to leave the IABP in place, remove the IABP, or remove and re-insert the IABP at a different location on the subject. For example, if the $rSO_2$ is above a first threshold, the processing equipment may determine to leave the IABP in place. If the $rSO_2$ drops below a first threshold, but is greater than a second threshold, the processing equipment may prompt the user to remove and re-insert the IABP at a different location on the subject. If the $rSO_2$ drops below the second threshold, the processing equipment may prompt the user to remove the IABP. In some embodiments, whether the IABP should remain in place, be removed, or be removed and re-inserted may be selected based on user input, for example, user input 182 of FIG. 1. For example, the processing equipment may decide to remove and re-insert the IABP based on user input indicating that the subject still requires the IABP. It will be understood that although the foregoing techniques of FIG. 8 have been described with reference to an IABP procedure, this is not limiting, and the clinical procedure may correspond to any other suitable cardiac assist procedures, including, for example, an extracorporeal membrane oxygenation (EMCO) procedure where the risk of embolization and resultant decrease in limb perfusion exists.

As described above with reference to step 514 of FIG. 5, in some embodiments, the processing equipment may detect an updated change in the $rSO_2$ of the subject based on the one or more corrective actions, and the processing equipment may update the status information based on the previously determined status information, the clinical information, and the updated change in the $rSO_2$ of the subject. For example, the processing equipment may detect an updated change in the $rSO_2$ of the subject, which indicates the $rSO_2$ is increasing. The processing equipment may determine updated status information indicative of a decreased risk of embolism (relative to the previously determined increased risk of embolism) based on the indication of increasing $rSO_2$, which may be indicative of increasing tissue perfusion, the clinical information, and the previously determined status information. In some embodiments, the processing equipment may display the updated status information, using, for example, display 184 of FIG. 1 or display 320 of FIG. 3.

It will be understood that the particular clinical procedures discussed in reference to FIGS. 6-8 are merely exemplary and are presented as non-limiting illustrations. It will be also be understood that the steps in each of the flow diagrams of FIGS. 6-8 are exemplary and that in some implementations, steps may be added, removed, omitted, repeated, reordered, modified in any other suitable way, or any combination thereof.

The foregoing is merely illustrative of the principles of this disclosure, and various modifications may be made by those skilled in the art without departing from the scope of this disclosure. The above-described embodiments are presented for purposes of illustration and not by way of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:

1. A physiological monitoring system comprising:
light drive circuitry configured for generating a light drive signal configured to cause one or more light sources to emit a plurality of light signals, wherein the plurality of light signals corresponds to a plurality of wavelengths of light;
one or more signal inputs configured for:
receiving a first plurality of light signals that have been attenuated by a first region of a subject, wherein the first plurality of light signals corresponds to the plurality of wavelengths of light;
receiving a second plurality of light signals that have been attenuated by a second region of the subject, wherein the second plurality of light signals corresponds to the plurality of wavelengths of light; and
receiving clinical information that indicates that the subject is undergoing an infusion pump procedure for sodium nitroprusside administration; and
one or more processors configured for:
monitoring regional blood oxygen saturation ($rSO_2$) of the subject based on the first received plurality of light signals and the second received plurality of light signals;
detecting a change in the $rSO_2$ of the subject;
determining status information for the subject that indicates an increased risk of cyanide toxicity associated with the infusion pump procedure when (a) the clinical information indicates that the subject is undergoing an infusion pump procedure and (b) the detected change in the $rSO_2$ of the subject exceeds a threshold; and
triggering an action based on the status information.

2. The system of claim 1, wherein triggering an action comprises outputting an alert signal indicative of the increased risk.

3. The system of claim 2, wherein triggering an action comprises prompting one or more corrective actions for reducing the increased risk.

4. The system of claim 3, wherein the one or more corrective actions comprise changing the administration dosage of sodium nitroprusside.

5. The system of claim 3, wherein the one or more corrective actions comprise terminating the administration of sodium nitroprusside and substituting an alternative vasodilator.

6. The system of claim 3, further comprising a display configured for displaying the one or more corrective actions.

7. The system of claim 6, wherein the one or more processors are further configured for:
selecting at least one of the one or more corrective actions for reducing the increased risk based on user input; and
performing the at least one selected corrective action.

8. The system of claim 3, wherein triggering an action comprises automatically performing the one or more corrective actions for reducing the increased risk.

9. The system of claim 8, wherein the one or more corrective actions comprise changing the administration dosage of sodium nitroprusside.

10. The system of claim 8, wherein the one or more corrective actions comprise terminating the administration of sodium nitroprusside and substituting an alternative vasodilator.

11. The system of claim 8, wherein the one or more processors are further configured for:
selecting at least one of the one or more corrective actions based on the severity of the increased risk; and
automatically performing the at least one selected corrective action.

12. The system of claim 8, wherein the one or more processors are further configured for:
detecting an updated change in the $rSO_2$ of the subject based on the one or more corrective actions; and
updating the status information based on the previously determined status information, the clinical information, and the updated change in the $rSO_2$ of the subject, wherein the updated status information is indicative of a decreased risk of cyanide toxicity for the subject;
the system further comprising a display configured for displaying the updated status information.

13. The system of claim 1, wherein the one or more signal inputs comprises a user input configured for receiving the clinical information from a user.

14. The system of claim 1, wherein the one or more signal inputs comprises an input configured for receiving the clinical information from a hospital information system.

15. The system of claim 1, wherein the one or more signal inputs comprises an input configured for receiving the clinical information from an infusion pump used in the infusion pump procedure.

16. The system of claim 1, further comprising a display configured for displaying the status information.

17. A physiological monitoring system comprising:
a signal input configured for receiving clinical information for a subject that indicates that the subject is undergoing a clinical procedure that affects a circulatory system of the subject; and
one or more processors configured for:
monitoring regional blood oxygen saturation ($rSO_2$) in a region of the subject that is affected by the clinical procedure;
detecting one or more changes in the $rSO_2$ in the region of the subject;
determining status information associated with the subject that indicates an increased risk of a physiological event caused by the clinical procedure when (a) the one or more changes in the $rSO_2$ in the region of the subject exceeds a threshold and (b) the clinical information indicates that the subject is undergoing the clinical procedure; and
triggering an action based on the status information.

18. The system of claim 17, wherein:
the clinical information indicates that the subject is undergoing an infusion pump procedure for sodium nitroprusside administration; and
the status information indicates a risk of cyanide toxicity.

19. The system of claim 17, wherein triggering an action comprises outputting an alert signal indicative of the increased risk.

20. The system of claim 17, wherein triggering an action comprises automatically performing one or more corrective actions for reducing the increased risk.

* * * * *